(12) United States Patent
Scarpone

(10) Patent No.: US 10,470,872 B1
(45) Date of Patent: Nov. 12, 2019

(54) IMPLANTABLE ARTICLES FOR ATTACHING TENDONS AND/OR LIGAMENTS TO BONE AND/OR CARTILAGE, ASSEMBLIES THEREOF, AND METHODS OF USE THEREOF

(71) Applicant: Michael A. Scarpone, Bloomingdale, OH (US)

(72) Inventor: Michael A. Scarpone, Bloomingdale, OH (US)

(73) Assignee: Michael A. Scarpone, Bloomingdale, OH (US)

( * ) Notice: Subject to any disclaimer, the term of this patent is extended or adjusted under 35 U.S.C. 154(b) by 0 days.

(21) Appl. No.: 16/381,503

(22) Filed: Apr. 11, 2019

Related U.S. Application Data

(63) Continuation-in-part of application No. 15/482,711, filed on Apr. 7, 2017, now abandoned, and a continuation-in-part of application No. 15/482,696, filed on Apr. 7, 2017.

(60) Provisional application No. 62/319,783, filed on Apr. 7, 2016, provisional application No. 62/319,308, filed on Apr. 7, 2016.

(51) Int. Cl.
*A61F 2/08* (2006.01)
*B33Y 80/00* (2015.01)

(52) U.S. Cl.
CPC .............. *A61F 2/0811* (2013.01); *B33Y 80/00* (2014.12); *A61F 2002/0817* (2013.01); *A61F 2002/0858* (2013.01)

(58) Field of Classification Search
CPC . A61B 17/7097; A61B 17/8855; A61B 17/84; A61B 17/864; A61B 17/8645; A61F 2/0811
See application file for complete search history.

(56) References Cited

U.S. PATENT DOCUMENTS

2012/0029578 A1* 2/2012 Suh .................... A61B 17/7035
606/309

\* cited by examiner

*Primary Examiner* — Andrew Yang
(74) *Attorney, Agent, or Firm* — K&L Gates LLP

(57) ABSTRACT

An implantable article for attaching tendons and/or ligaments to bone and/or cartilage, assemblies thereof, and methods of use thereof are provided. The implantable article is configured for attaching at least one of a tendon and a ligament to at least one of bone and cartilage. The article comprises a membrane comprising a biological material that promotes cell growth. The membrane comprises an open end configured to receive a cell growth mixture, a closed end configured to be attached to the at least one of bone and cartilage, and a cavity extending from the open end to the closed end. The cavity is configured to receive the cell growth mixture from the open end.

20 Claims, 20 Drawing Sheets

US 10,470,872 B1

IMPLANTABLE ARTICLES FOR ATTACHING TENDONS AND/OR LIGAMENTS TO BONE AND/OR CARTILAGE, ASSEMBLIES THEREOF, AND METHODS OF USE THEREOF

CROSS-REFERENCE TO RELATED APPLICATIONS

The present application is a continuation-in-part of U.S. patent application Ser. No. 15/482,711, which was filed on Apr. 7, 2017, and which claims priority to U.S. Provisional Patent Application No. 62/319,783, which was filed on Apr. 7, 2016; and a continuation-in-part of U.S. patent application Ser. No. 15/482,696, which was filed on Apr. 7, 2017, and which claims priority to U.S. Provisional Patent Application No. 62/319,308, which was filed on Apr. 7, 2016. The contents of each are hereby incorporated by reference into this specification.

FIELD

The present application relates to implantable articles for attaching tendons and/or ligaments to bone, assemblies thereof, and methods of use thereof.

BACKGROUND

A tendon and/or a ligament can be degraded due to injury, infection, and/or disease. The degraded tendon and/or ligament may need to be repaired by a medical procedure to remedy the injury, infection, and/or disease. There are challenges with current medical procedures to repair tendons and/or ligaments.

SUMMARY

The present disclosure provides an implantable article configured for attaching at least one of a tendon and a ligament to at least one of bone and cartilage. The article comprises a membrane comprising a biological material that promotes cell growth. The membrane comprises an open end configured to receive a cell growth mixture, a closed end configured to be attached to the at least one of bone and cartilage, and a cavity extending from the open end to the closed end. The cavity is configured to receive the cell growth mixture from the open end.

The present disclosure also provides a method for repairing at least one of a tendon and a ligament. The method comprises contacting an implantable article configured to attach at least one of a tendon and a ligament to at least one of bone and cartilage, with the at least one of a tendon and a ligament. The article comprises a membrane comprising a biological material that promotes cell growth. The membrane comprises an open end configured to receive a cell growth mixture, a closed end configured to be attached to the at least one of bone and cartilage, and a cavity extending from the open end to the closed end. The cavity is configured to receive the cell growth mixture from the open end. The method comprises introducing the cell growth mixture into the cavity of the implantable article and attaching the implantable article to at least one of bone and cartilage with an anchor.

The present disclosure also provides an implantable article configured for attaching at least one of a tendon and a ligament to at least one of bone and cartilage. The article comprises a first membrane, a second membrane, and a flange connecting the first membrane to the second membrane. The first membrane comprises a biological material that promotes cell growth. The first membrane comprises a first open end configured to receive a cell growth mixture, a first closed end configured to be attached to the at least one of bone and cartilage, and a first cavity extending from the first open end to the first closed end. The first cavity is configured to receive the cell growth mixture from the first open end. The second membrane comprises a first open end configured to receive the cell growth mixture, a second closed end configured to be attached to the at least one of bone and cartilage, and a second cavity extending from the second open end to the second closed end. The second cavity is configured to receive the cell growth mixture from the second open end.

The present disclosure also provides an implantable article configured for attaching at least one of a tendon and a ligament to at least one of bone and cartilage. The article comprises an insertion tip, a reservoir, and a tube. The insertion tip comprises a biological material that promotes cell growth. The insertion tip comprises an open end configured to receive a cell growth mixture, a closed end configured to be attached to the at least one of muscle, a tendon, and a ligament, and a cavity extending from the open end to the closed end. The cavity is configured to receive the cell growth mixture from the open end. The reservoir comprises the biological material. The reservoir is in fluid communication with the insertion tip and the reservoir is configured to receive the cell growth mixture. The tube is in fluid communication with the reservoir. The tube is configured to receive the cell growth mixture and be attached to at least one of bone and cartilage.

It is understood that the inventions described in this specification are not limited to the examples summarized in this Summary. Various other aspects are described and exemplified herein.

BRIEF DESCRIPTION OF THE DRAWINGS

The features and advantages of the examples, and the manner of attaining them, will become more apparent, and the examples will be better understood by reference to the following description of examples taken in conjunction with the accompanying drawings, wherein.

Corresponding reference characters indicate corresponding parts throughout the several views. The exemplifications set out herein illustrate certain examples, in one form, and such exemplifications are not to be construed as limiting the scope of the examples in any manner.

DETAILED DESCRIPTION

Figure 1:
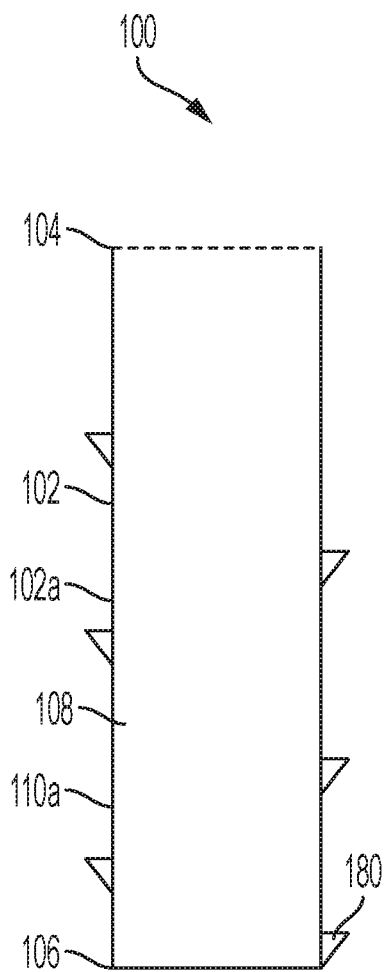
FIG. 1 illustrates a schematic diagram of an implantable article according to the present disclosure.

Various examples of the present disclosure will now be described to provide an overall understanding of the principles of the composition, function, manufacture, and use of the compositions and methods disclosed herein. One or more examples are illustrated in the accompanying drawings. Those of ordinary skill in the art will understand that the compositions, articles, and methods specifically described herein and illustrated in the accompanying drawings are non-limiting exemplary examples and that the scope of the various examples of the present invention is defined solely by the claims. The features illustrated or described in connection with one exemplary example may be combined with the features of other examples. Such modifications and variations are intended to be included within the scope of the present invention.

Reference throughout the specification to "various examples," "some examples," "one example," "an example," or the like, means that a particular feature, structure, or characteristic described in connection with the example is included in at least one example. Thus, appearances of the phrases "in various examples," "in some examples," "in one example," "in an example," or the like, in places throughout the specification are not necessarily all referring to the same example. Furthermore, the particular features, structures, or characteristics may be combined in any suitable manner in one or more examples. Thus, the particular features, structures, or characteristics illustrated or described in connection with one example may be combined, in whole or in part, with the features, structures, or characteristics of one or more other examples without limitation. Such modifications and variations are intended to be included within the scope of the present examples.

Any numerical range recited in this specification describes all sub-ranges of the same numerical precision (i.e., having the same number of specified digits) subsumed within the recited range. For example, a recited range of "1.0 to 10.0" describes all sub-ranges between (and including) the recited minimum value of 1.0 and the recited maximum value of 10.0, such as, for example, "2.4 to 7.6," even if the range of "2.4 to 7.6" is not expressly recited in the text of the specification. Accordingly, the Applicant reserves the right to amend this specification, including the claims, to expressly recite any sub-range of the same numerical precision subsumed within the ranges expressly recited in this specification. All such ranges are inherently described in this specification such that amending to expressly recite any such sub-ranges will comply with the written description, sufficiency of description, and added matter requirements.

Also, unless expressly specified or otherwise required by context, all numerical parameters described in this specification (such as those expressing values, ranges, amounts, percentages, and the like) may be read as if prefaced by the word "about," even if the word "about" does not expressly appear before a number. Additionally, numerical parameters described in this specification should be construed in light of the number of reported significant digits, numerical precision, and by applying ordinary rounding techniques. It is also understood that numerical parameters described in this specification will necessarily possess the inherent variability characteristic of the underlying measurement techniques used to determine the numerical value of the parameters.

Notwithstanding that numerical ranges and parameters setting forth the broad scope of the invention are approximations, numerical values are set forth in the specific examples are reported precisely as possible. Any numerical value, however, inherently contains certain errors necessarily resulting from the standard variation found in their respective testing measurements.

The grammatical articles "a," "an," and "the," as used in this specification, including the claims, are intended to include "at least one" or "one or more" unless otherwise indicated. Thus, the articles are used in this specification to refer to one or more than one (i.e., to "at least one") of the grammatical objects of the article. By way of example, "a component" means one or more components, and thus, possibly more than one component is contemplated and can be employed or used in an implementation of the described compositions, coatings, and processes. Nevertheless, it is understood that use of the terms "at least one" or "one or more" in some instances, but not others, will not result in any interpretation where failure to use the terms limits objects of the grammatical articles "a," "an," and "the" to just one. Further, the use of a singular noun includes the plural, and the use of a plural noun includes the singular, unless the context of the usage requires otherwise.

A tendon can be coupled directly to a muscle and attaches the muscle to another structure such as, for example, a bone and/or cartilage. A ligament can attach non-muscle tissues, such as, for example, bones and/or cartilage, to other non-muscle tissues. A tendon and a ligament can comprise flexible and non-stretchable bundles of collagen. As used herein, the term "attachment structure" refers to a tendon, a ligament, or both a tendon and a ligament. As used herein, the term "base structure" refers to bone, cartilage, or both bone and cartilage.

An attachment structure can become degraded, due to injury, infection, and/or disease as a result of, for example, a traumatic force and/or a gradual deterioration. The degradation can be a partial or complete rupture of the attachment structure. For example, a rupture of an attachment structure can be a partial or complete detachment of the attachment structure from a corresponding base structure or otherwise weakening, loosening, or disrupting, of the attachment structure at a location where the attachment structure was previously attached to the corresponding base structure. Some ruptures may require a medical procedure in order to effectively and/or efficiently repair the attachment structure as the attachment structure may only have a limited ability to repair (e.g., regenerate, regrow, reattach) on its own. For example, an attachment structure may have a lower cell density and blood supply than muscles and/or internal organs which can make the repair of the attachment structure take longer than a muscle and/or internal organ.

Thus, articles for attaching an attachment structure to a base structure, assemblies thereof, and methods of use thereof are provided. The articles, assemblies, and methods as described in the disclosure can repair various attachment structures. The articles, assemblies, and methods can repair attachment structures in a joint, such as, for example, a shoulder joint, a hip joint, an elbow joint, a knee joint, an ankle joint, and/or a wrist joint. In various examples, the articles, assemblies, and methods of the present disclosure can repair the anterior cruciate ligament (ACL) in the knee joint and/or the tendon which attaches the supra-spinatus muscle to the humerus bone in the shoulder joint.

As illustrated in FIG. 1, an implantable article 100 comprising a membrane 102 is provided. The membrane 102 can comprise an open end 104, a closed end 106, and a cavity 108 extending from the open 104 to the closed end 106. The membrane 102 can be configured to attach to a base structure, an attachment structure, and/or a muscle. The membrane 102 can be dissolved and/or reabsorbed by a base structure, attachment structure, and/or other surrounding elements. The membrane 102 can comprise biological material that promotes cell growth (e.g., repair of the attachment structure), such as, for example, at least one of a placental membrane, a collagen membrane, a carbohydrate matrix, a biocompatible polymer membrane, and a biologically derived membrane. The biological material can comprise the Atreon Bti scaffold-based product available from Atreon Orthopedics Columbus, Ohio. In various examples, the biological material can promote mammalian cell growth and soft tissue repair. The membrane 102 can be a scaffold.

A placental membrane can comprise interface tissues obtained from a placenta including the umbilical cord and amniotic sac. The biologically derived membrane can comprise synthetic collagenous meshes bonded to natural membranes (e.g., skin, placental membranes) by using biocompatible adhesives. For example, the biologically derived membrane can comprise at least one of the crosslinked collagen mucopolysaccharide composite material as described in U.S. Pat. No. 4,060,081 to Yannas et al., the multilayer membrane as described in U.S. Pat. No. 4,060,081 to Yannas et al., and a cell carrying collagenous membrane. In various examples, the membrane 102 can comprise a placental membrane attached to a collagen membrane with a soft and pliable interface of biocompatible adhesive, such as, for example, polyacrylate, between them the placental membrane and the collagen membrane. The collagen membrane can comprise chemically crosslinked collagen fibers. The biocompatible polymer can be polyvinyl alcohol, poly acrylamide, poly acrylate, and polyethylene glycol.

The membrane 102 can be formed by various processes, such as, for example, at least one of cutting, sewing, fusing, molding, pressing, and additive manufacturing. For example, in order to form the membrane 102, a sheet of biological membrane can be formed in a desired shape. Thereafter, the sheet can be rolled into a substantially cylindrical shape and in various examples, an overlapping portion of the sheet in the substantially cylindrical shape can be sealed. In various other examples, the overlapping portion is not sealed. An end of the substantially cylindrical shape can be sealed by, for example, folding the end over, fusing the end, and/or sewing the end in order to form the membrane 102. In yet another example, the membrane 102 can be additively manufactured into the desired configuration and shape. The membrane 102 can be a single piece or multiple pieces.

The closed end 106 of the membrane 102 can comprise a bore suitable for receiving a guide wire. The bore of the closed end 106 can be smaller than a diameter of the open end 104 and the bore of the closed end 106 can be occluded by a base structure and/or an attachment structure in order to retain a cell growth mixture within the cavity 108.

The membrane 102 can comprise various levels of density, porosity, and/or permeability, which can affect the release of a cell growth mixture within the cavity 108 to the base structure, the attachment structure, and/or other surrounding elements. For example, the membrane 102 can enable 75 percent of the cell count of the cell growth mixture to diffuse through the membrane 102 from the cavity 108 after a day, such as, for example, after a week, after at least 2 weeks, after at least 4 weeks, after at least 6 weeks, after at least 8 week, after at least 10 weeks, after at least 12 weeks, or after at least 16 weeks. The membrane 102 can enable 75 percent of the cell count of the cell growth mixture to diffuse through the membrane 102 from the cavity 108 after 16 weeks or less, after 12 weeks or less, after 10 weeks or less, after 8 weeks or less, after 6 weeks or less, after 4 weeks or less, after 2 weeks or less, or after one week or less. The membrane 102 can enable 75 percent of the cell count of the cell growth mixture to diffuse through the membrane 102 in a range of 1 day to 16 weeks, such as, for example, 1 week to 10 weeks, or 2 weeks to 6 weeks.

The cell growth mixture can promote the repair of the attachment structure, such as, for example, growth of collagen fibers within the attachment structure. The cell growth mixture can comprise at least one of stem cells, platelets, and spun fat. Stem cells can form into new and regenerated tissues and can be harvested from, for example, bone marrow. Thus, the cell growth mixture can comprise bone marrow. In various examples, the stem cells can comprise stromal precursor cells. In various examples, the cell growth mixture can comprise stromal precursor cells and spun fat as described in U.S. Patent Publication No. 2012/0156177.

The platelets can release hormones, growth factors, and/or other molecules that signal to other repair cells the location of the degradation in the attachment structure and the need to repair the degradation. The platelets can be obtained from platelet rich plasma. Thus, the cell growth mixture can comprise platelet rich plasma. In various examples, the cell growth mixture can also comprise additives, such as, for example, growth factors. In various examples, the cell growth mixture can facilitate the formation of collagen fibers and/or facilitate deposition of collagen fibers onto the degraded attachment structure. The formation and/or deposition of the collagen fibers can facilitate repair of the degraded attachment structure.

Bone marrow can be harvested from various bones in a human and/or an animal. For example, a harvesting device, such as, for example, a trocar, can be penetrated into a bone. The trocar can penetrate through the cortex bone, the spongy bone, and into the bone marrow. A suction device (e.g., an aspirator) can be used to remove (e.g., aspirate) a desired quantity of bone marrow out of the bone through the trocar. The harvested bone marrow can be in a semi-liquefied form and can be used in the cell growth mixture. The harvested bone marrow can be from a patient that will receive the implantable device 100, a different patient, a cadaver, and/or an animal.

Referring again to FIG. 1, the open end 102 of the membrane 102 can be configured to receive the cell growth mixture, and transport the cell growth mixture to the cavity 108 and, in various examples, the closed end 106. For example, the open end 102 can comprise a diameter configured to receive the cell growth mixture from an insertion guide, such as, for example, a cannula, a catheter (e.g., balloon catheter), a syringe, and/or a trocar.

The implantable article 100 and the closed end 106 can be configured to be attached to a base structure and/or an attachment structure. For example, the closed end 106 can be attached to the base structure by a staple, a pin, a fastener (e.g., a screw), a suture, the dowel, and an adhesive.

In various examples, the open end 102 can be configured to receive a dowel and transport the dowel to the cavity 108 and, in various examples, the closed end 106. The dowel can comprise, for example, at least one of bone (e.g., cortex bone, spongy bone), a biocompatible polymer that can be dissolved and/or reabsorbed by a body of the subject, and a biocompatible mineral. The biocompatible polymer can comprise polyether ether ketone (e.g., PEEK). The biocompatible mineral can comprise calcium phosphate containing mineral (e.g., apatite). The biocompatible mineral can be manufactured by facilitating crystal growth of the mineral to a desired shape, sintering a powder of the mineral into a desired shape, and/or using a biocompatible glue to join a powder of the mineral together.

The dowel can be manufactured and/or harvested from various bones in a human and/or an animal, such as, for example a pelvic bone and/or a femur. The dowel can be harvested by using a harvesting device, such as, for example, a trocar in a procedure similar to how bone marrow was harvested as described above. The dowel can be harvested from a patient that will receive the implantable device 100, a different patient, a cadaver, and/or an animal. The dowel can be subjected to various processes to minimize the risk of immune rejection, such as, for example, removal of antigens that may provoke an immune response (e.g., chemical treatments). In various other examples, the dowel can be additively manufactured. In various examples, the dowel can comprise cortex bone from an outer portion of a pelvic bone at one end and spongy bone that was disposed intermediate the cortex bone and bone marrow at another end.

The dowel can comprise a generally cylindrical shape, a generally elliptical shape, or a polygon shape. In various examples where the dowel comprises a generally cylindrical shape, the dowel can have a diameter of 0.5 inches or less, such as, for example, 0.25 inch or less, 0.125 inch or less, 0.1 inch or less, 0.083 inch or less, 0.0625 inch or less, or 0.056 inch or less. The dowel can have a diameter of 0.01 inch or greater, such as, for example, 0.056 inch or greater, 0.0625 inch or greater, 0.083 inch or greater, 0.1 inch or greater, 0.125 inch or greater, or 0.25 inch or greater. The dowel can have a diameter in a range of 0.01 inch to 0.5 inch, such as, for example, 0.1 inch to 0.25 inch or 0.0625 inch to 0.25 inch. A dowel harvested with a trocar can have a diameter substantially similar to an internal diameter of the trocar.

The dowel can have a length of 0.01 inch or greater, such as, for example, 0.05 inch or greater, 0.1 inch or greater, 0.25 inch or greater, 0.5 inch or greater, 0.75 inch or greater, or 1 inch or greater. The dowel can have a length of 2 inch or less, such as, for example, 1 inch or less, 0.75 inch or less, 0.5 inch or less, 0.25 inch or less, 0.1 inch or less, or 0.05 inch or less. The dowel can have a length in a range of 0.01 inch to 2 inch, such as, for example, 0.25 inch to 1 inch or 0.25 to 0.75 inch. In various examples, the dowel can be dynamically trimmed to accommodate a bore formed in the base structure during a surgical procedure. The dowel can be pressed into a bore formed in a base structure for a friction fit.

The membrane 102 can comprise a generally cylindrical shape, a generally elliptical shape, and/or a polygon shape. The shape and/or permeability of the membrane 102 can enable cell growth mixture contained within the cavity to efficiently diffuse through the membrane 102 and into the surrounding environment, such as, for example, a base structure, an attachment structure, and/or other surrounding elements. The shape of the membrane 102 can be configured to dispose a desired quantity of cell growth mixture proximal and/or adjacent to the attachment structure which can increase the rate at which collagen fiber can regrow in the attachment structure. For example, the membrane 102 can enable efficient diffusion of the cell growth mixture in an interface area where the attachment structure may have ruptured. In various examples, the membrane 102 can comprise an expandable portion 110a configured to increase in size responsive to the cell growth mixture entering the cavity 108. The increase in size of the expandable portion 110a can increase the surface area of the membrane 102 which can increase diffusion of the cell growth mixture, a contact surface area between the membrane 102 and a base structure and/or attachment structure, and a volume of the cavity 108. In various examples, the membrane 102 can comprise at least two expandable portions including expandable portion 110a.

The membrane 102 can be configured to be attached in an attachment structure and/or other resist removal. For example, the membrane 102 can comprise retainers 180 on an outer surface 102a. The retainers 180 can be, for example, a protrusion, a barb, a spike, a hook, a bristle, a prong, and a spur. The retainers 180 can be oriented at an oblique angle relative to the membrane 102 away from a direction of insertion of the implantable article 100 to enable facile insertion of the membrane 102 into a base structure, an attachment structure, and/or other surrounding elements. The oblique angle of the retainers 180 can inhibit or prevent removal of the membrane 102 from the base structure, the attachment structure, and/or other surrounding elements. In various examples, a membrane 102 comprising retainers 180 on the outer surface 102a can comprises a texture similar to shark skin. The retainers 180 can comprise biological material. The retainers 180 can comprise the same material as the membrane 102 or a different material than the membrane 102.

The retainers 180 can be formed integrally with the membrane 102 and/or in a secondary process. For example, the retainers 180 can be formed by at least one of molding, additively manufacturing, cutting, fusing, and machining. The membrane 102 can be subjected to an accretion process, such as, for example, vapor deposition and/or crystal growth. Vapor deposition can comprise passing a fluid over a surface 102a of the membrane 102 in a unidirectional manner so that the flow of the fluid would control crystal growth in a desired direction. In various other examples, the retainers 180 can be cut into the membrane 102. In various examples, the retainers 180 can be molded integrally with the membrane 102.

Figure 2:
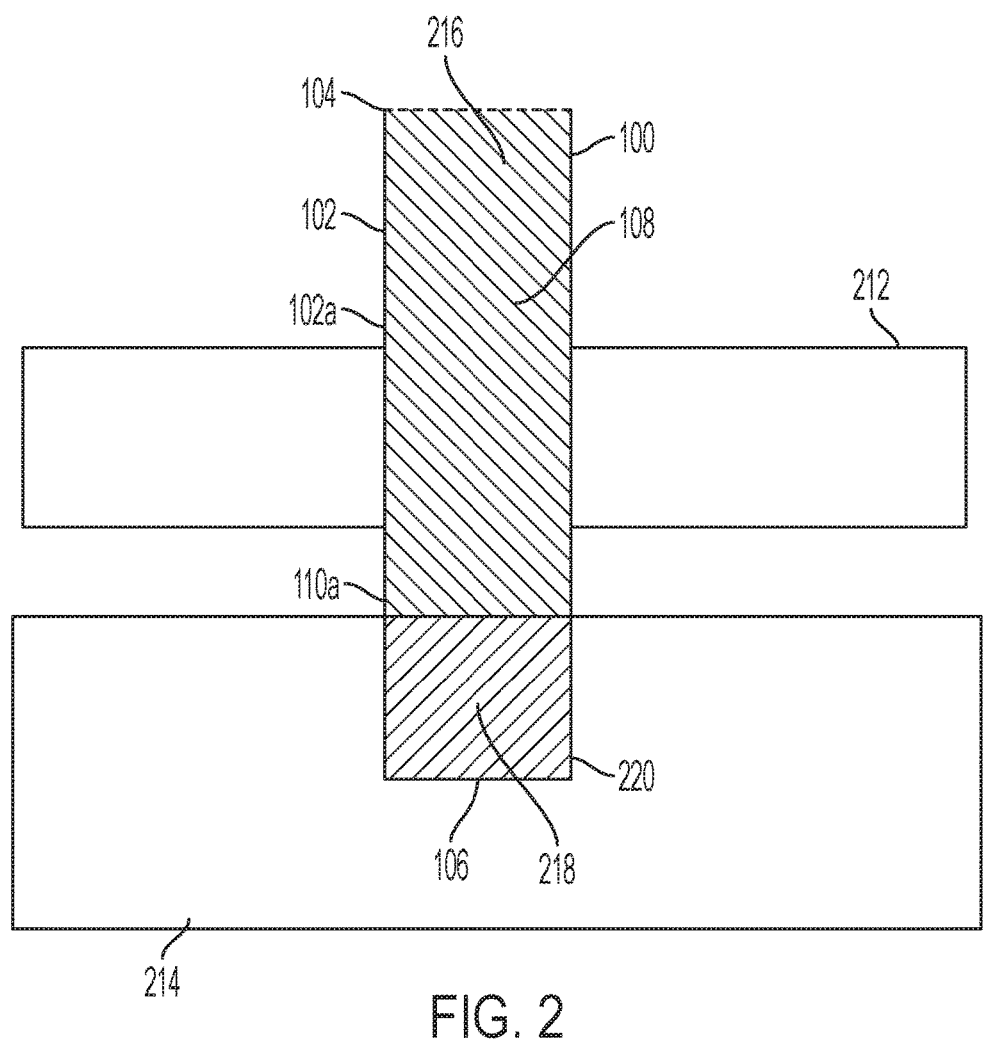
FIG. 2 illustrates a schematic diagram of an implantable article attached to a base structure and an attachment structure according to the present disclosure.

Referring to FIG. 2, the implantable article 100 can be inserted into an attachment structure 212 and attached to a base structure 214 by an anchor, such as, for example, a dowel 218. A bore 220 can be formed in the base structure 214 by, for example, drilling prior to insertion of the implantable article 100. The closed end 106 of the implantable article can be placed in the bore 220 and the dowel 218 can be passed through the open end 204 of the membrane 102 and advanced through the cavity 108 until the dowel 218 forms a friction fit between an assembly of the membrane 102 and dowel 218 and the bore 220. The friction fit can maintain a position of the implantable article 100 relative to the base structure 214. The dowel 218 can be substantially flush with a surface of the base structure 214, the dowel may protrude slightly from the surface of the base structure 214, or the dowel can be slightly recessed within the base structure 214.

In various examples, the dowel 218 engages the closed end 106 of the implantable article 100. In various examples where the dowel 218 comprises cortex bone and spongy bone, the dowel 218 can be oriented such that a cortex bone portion of the dowel 218 is more proximal to the closed end 106 than a spongy bone portion of the dowel 218. In various examples, a secondary anchor can be driven into the dowel 218 to expand a diameter of the dowel to increase a strength of the friction fit. In various other examples, implantable article 100 can be attached to the base structure 214 by an anchor that may not comprise a dowel.

Cell growth mixture 216 can be introduced into the cavity 108 of the implantable article 100 through the open end 104 of the membrane 102. The introduction of the cell growth mixture 216 to the cavity 108 can be performed within minimal, if any, formation of air bubbles with the cell growth mixture 216 as the cavity 108 is filled. For example, a tip of a insertion guide can be introduced into the cavity 108 until the tip of the insertion guide reaches the closed end 106 of the membrane 102 or in examples comprising a dowel 218, the dowel 218. Then cell growth mixture 216 can be introduced into the cavity 108 and, as the cavity 108 fills, the tip of the insertion device can be retracted from the cavity 108 such that the tip may be proximal to the fill level of cell growth mixture 216 in the cavity 108.

The implantable device 100 can be configured to repair various attachment structures. The repair of the attachment structure can position the closed end 106 of the implantable device 100 proximal to the base structure as shown in FIGS. 3A-G (e.g., a first orientation) or proximal to the attachment structure and/or muscle as shown in FIGS. 4A-E (e.g., a second orientation).

Figure 3A:
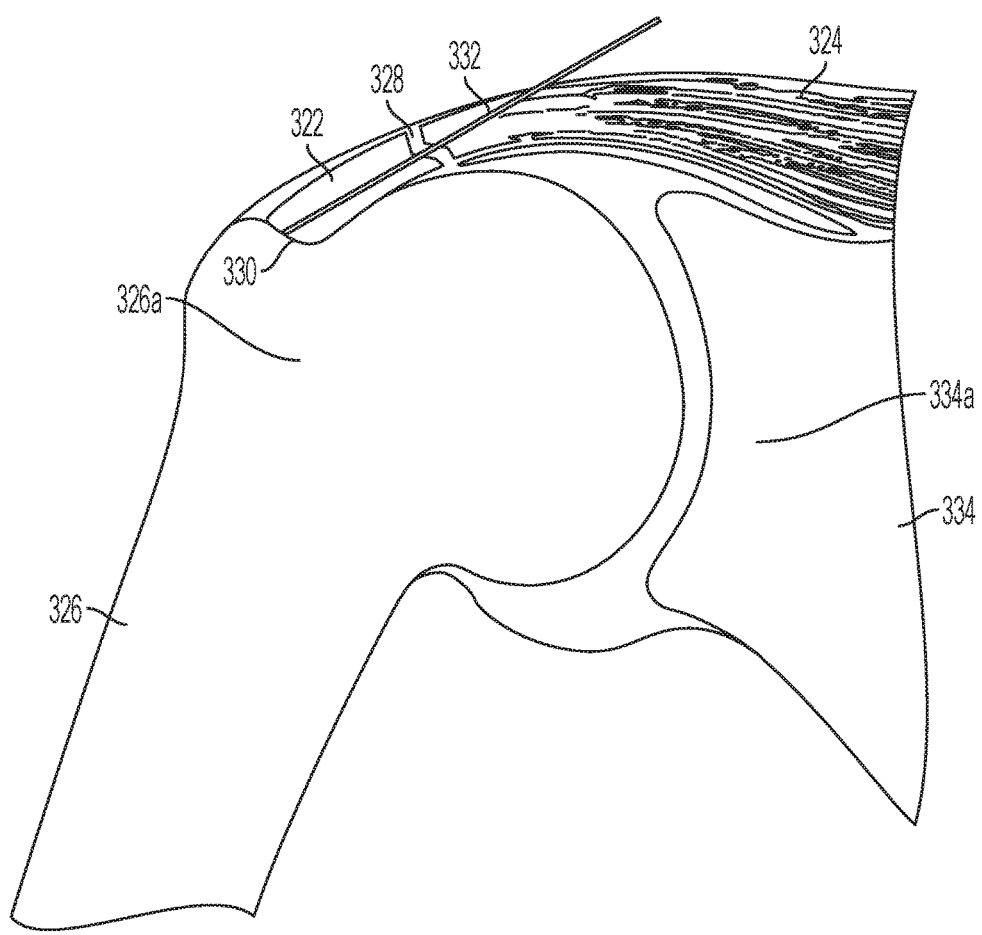
FIGS. 3A-G illustrate schematic diagrams of various steps in a method for repairing an attachment structure with the implantable article in a first orientation according to the present disclosure.

Referring to FIGS. 3A-G, the implantable article 100 can be configured to repair a tendon 322 connecting the corresponding supra-spinatus muscle 324 to the humerus 326. The tendon 322 is shown as ruptured at a location 328. As illustrated in FIG. 3A, the tendon 322 can be moved (e.g., pulled, pushed) until the tendon 322 is substantially aligned with an attachment location 330 on a humeral head 326a of the humerus 326. Various types of devices, such as, for example, pliers, clamps, sutures, and guidewires, can be used for moving the tendon 322. The attachment location 330 may vary depending on the extent and/or type of rupture to the tendon 322.

A distance that the tendon 322 may have to be moved can be changed by moving and/or orienting the humerus 326 such that the attachment location 330 is closer to a socket 334a of the scapula 334. For example, the humerus 326 can be rotated into an outward-extending position (not-shown) to reduce the distance that the tendon 322 may be need to be moved to be substantially aligned with the attachment location 330.

A guide wire 332 can be introduced into and through the tendon 322 and then to the attachment location 330 on the humerus 326. Optionally, the guide wire 332 can pass through the supra-spinatus muscle 324 prior to the tendon 322. The guide wire 332 can facilitate the insertion of the implantable device 100 in a desired position and/or orientation relative to the humerus 326 and the tendon 322.

Figure 3B:
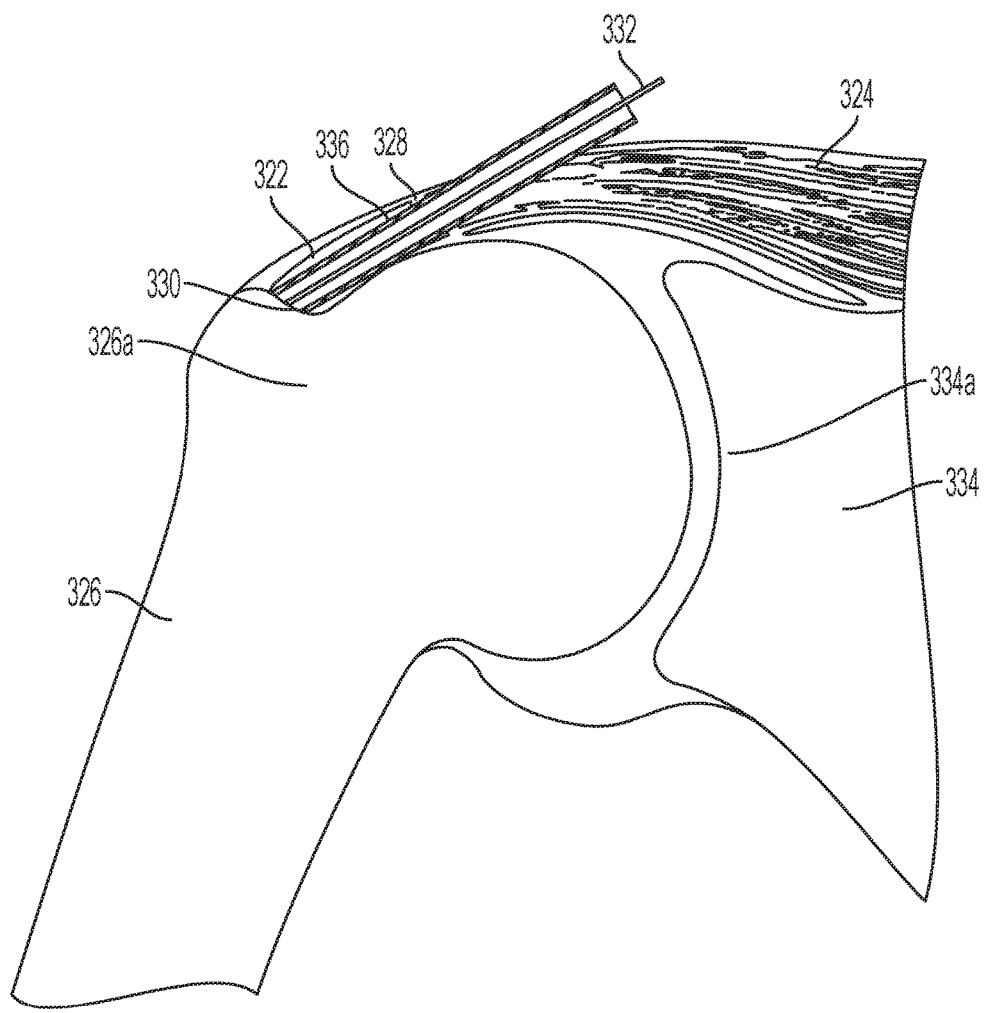

As illustrated in FIG. 3B, a dilator 336 can be substantially aligned with the guide wire 332 and advanced along the guide wire 332 in order to deform tissue surrounding the guide wire 332 including the tendon 322 in order to create a channel (not shown) configured to receive the implantable article 100. The dilator 336 can be removed from the guide wire 332 and the channel in the tissue can remain. In various examples, a second dilator (not shown) different than the dilator 336 can be substantially aligned with the guide wire 332 and advanced along the guide wire 332 in order to further deform the tissue surrounding the guide wire 332. For example, the second dilator can increase a diameter of the channel. In various examples, a balloon catheter can be substantially aligned with the guide wire 332 and advanced along the guide wire 332 in order to deform tissue surrounding the guide wire 332. The quantity of and/or types of devices used to create the channel may vary dependent on size of the tendon 322, size of the humerus 326, extent of the rupture, and/or a desired channel size or shape.

Figure 3C:
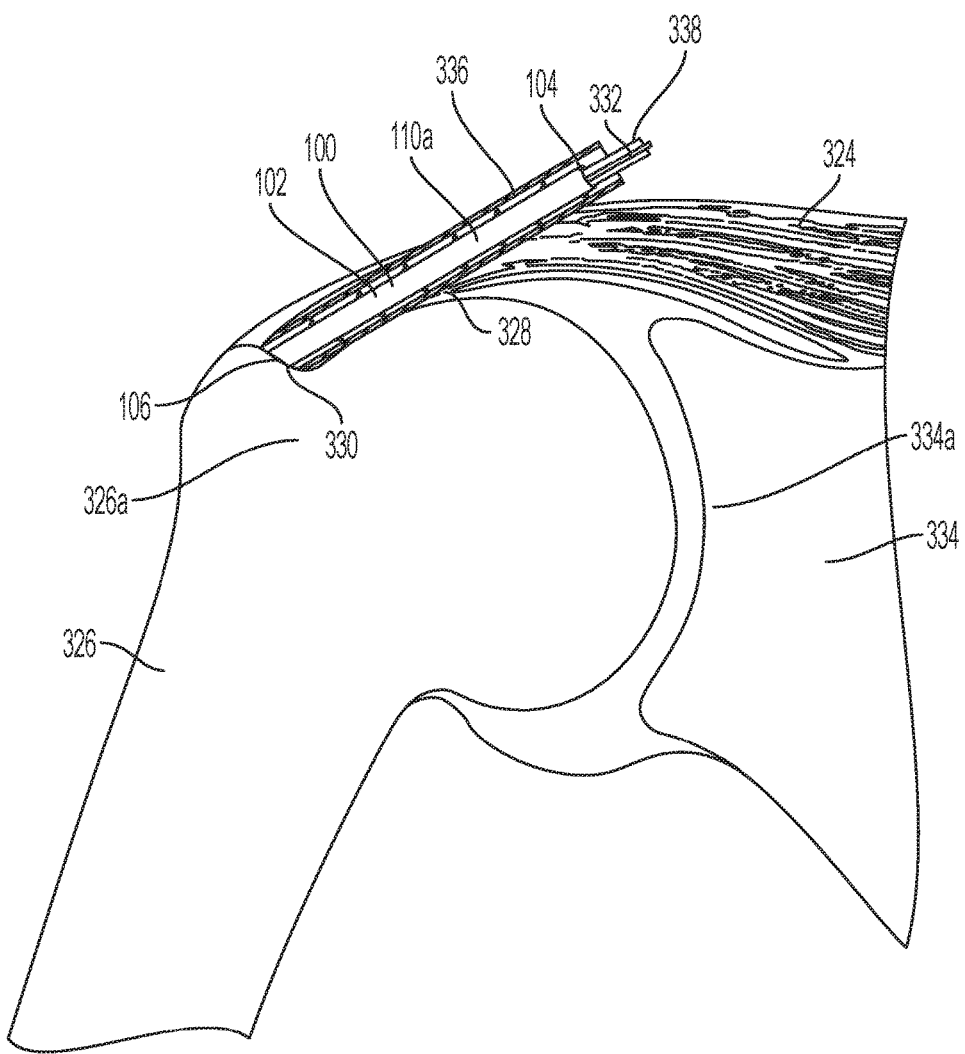

The dilator 336 can remain on the guide wire 332 and in the tissue while another device can be inserted within the dilator 336. As illustrated in FIG. 3C, an insertion guide 338 can be configured to introduce the implantable article 100 to the attachment location 330. The implantable article 100 can be disposed on a tip of the insertion guide 338 and the insertion guide 338 and implantable article 100 together can be advanced into the tendon 322 and proximal to the attachment location 330 utilizing the guide wire 332. The insertion guide 338 and implantable article 100 can be advanced through the dilator 336 and the dilator 336 can be removed thereafter. The insertion guide 338 can comprise an internal cavity configured to receive the guide wire 332 and the implantable article 100 can comprise a bore on the closed end 106 configured to receive the guide wire 332.

Figure 3D:
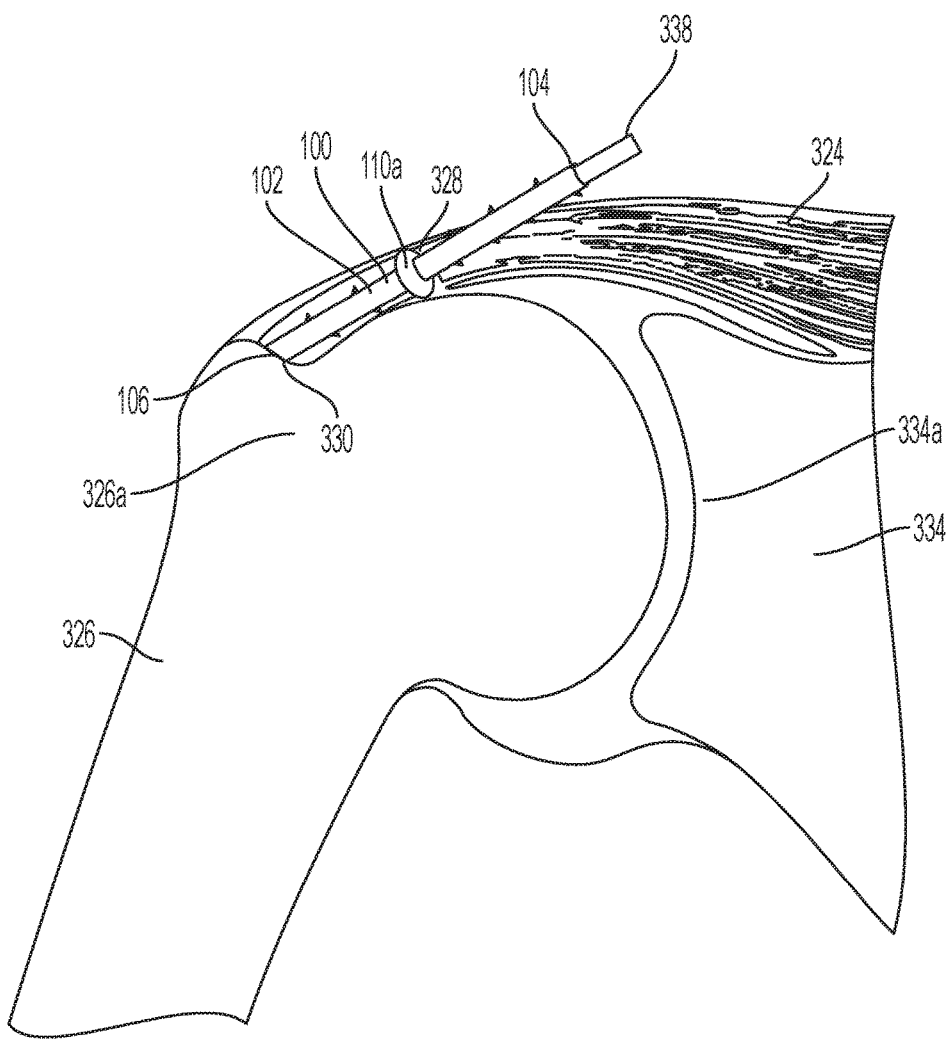

Upon inserting the implantable article 100 to a desired location, the guide wire 332 can be removed prior to an introduction of cell growth mixture into the cavity 108. Then, the cell growth mixture can be introduced into the cavity 108 of the implantable article 100 by the insertion guide 338. Upon introduction of the cell growth mixture to the cavity 108 of the membrane 102 of the implantable article 100, a size of the membrane 102 of the implantable article 100 can increase which can increase a friction fit of the membrane 102 and surrounding tissue, increase diffusion of cell growth mixture through the membrane 102, and/or increase a volume of the cavity 108. As shown in FIG. 3D, the expandable portion 110a can increase in size responsive to the cell growth mixture being introduced to the cavity 108 of the implantable article 100. In various examples, the expandable portion 110a can be comprise a diameter greater than a diameter of the membrane 102 prior to introduction of the cell growth mixture to the cavity 108. For example, the expandable portion 110a can be an enlarged portion of the membrane 102. In various examples, a dowel can be inserted into the implantable article 100 utilizing the insertion guide 338 prior to introducing the cell growth mixture into the cavity 108 of the implantable article 100. The dowel can attach the closed end 106 of the membrane 102 of the implantable article 100 to the humerus 326.

Figure 3E:
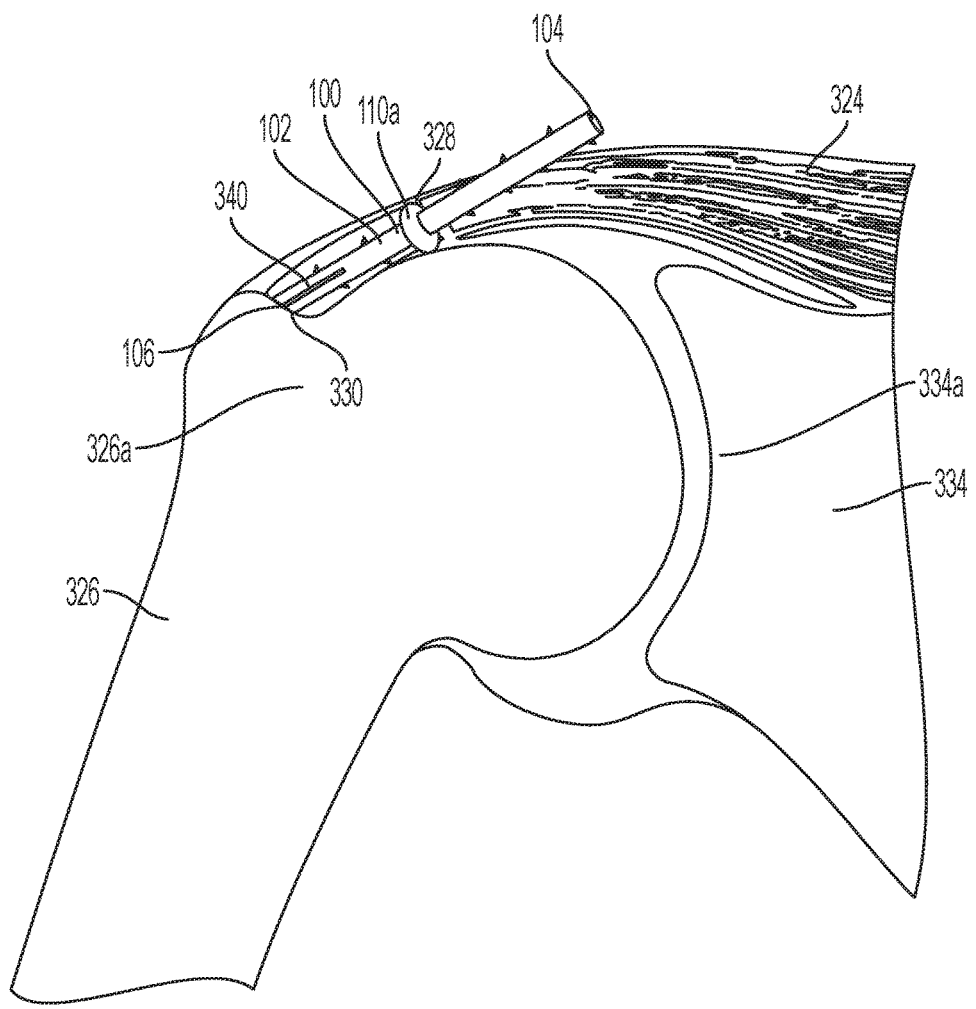

The membrane 102 of the implantable article 100 can be cut to a desired length. In various examples, the open end 104 of the implantable article 100 can be pressed up against the tendon 322 and/or the supra-spinatus muscle 324. As illustrated in FIG. 3E, the implantable article 100 can be attached to the humerus 326 by an anchor 340. The anchor 340 can be attached prior to, during, and/or after filling the implantable article with cell growth mixture. The anchor 340 can attach the closed end 106 of the implantable article to the humerus 346. Additional anchors can be installed as needed to attach the implantable article to the tendon 322 and/or the humerus 346; or attach the tendon 322 to the humerus 346.

Figure 3F:
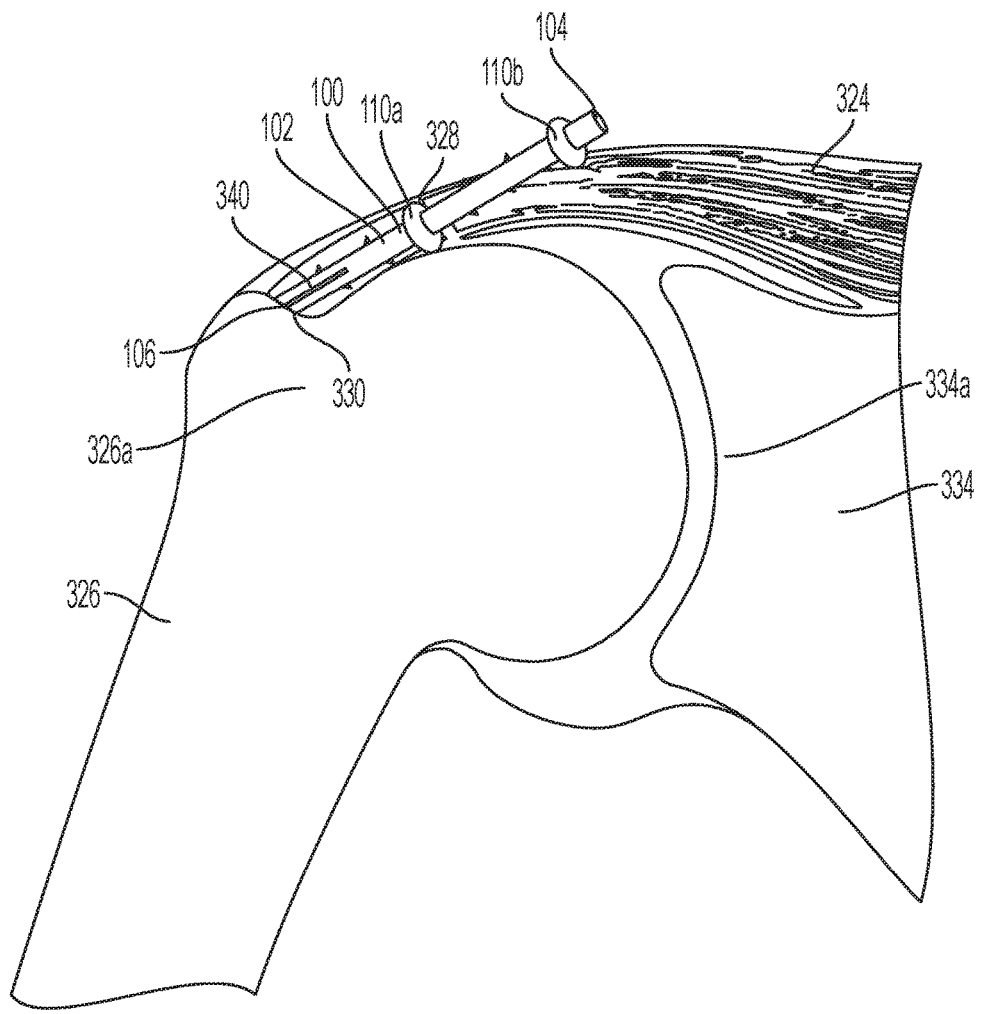
Figure 3G:
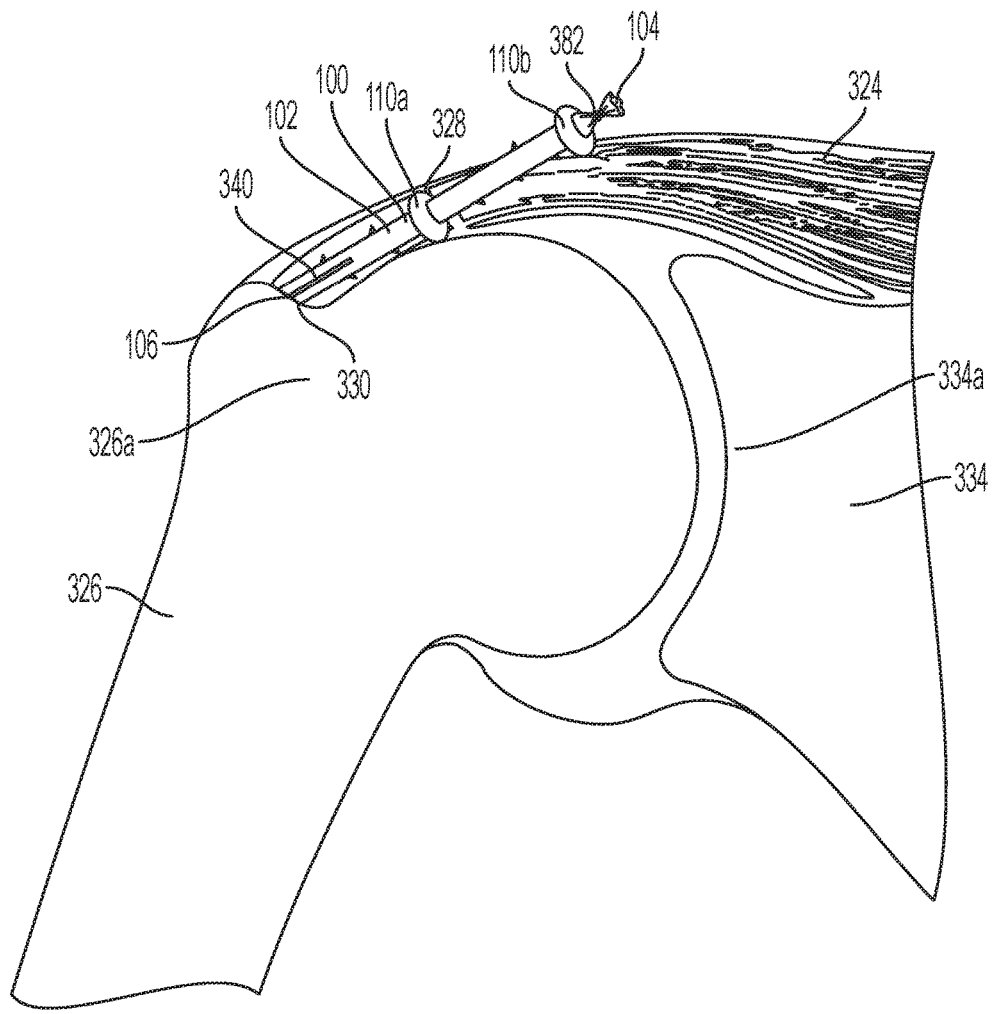

In various examples, the open end 104 of the implantable article 100 can be sealed. For example, as shown in FIG. 3G, the open end 104 can be sealed with a ring 382 (e.g., a PEEK ring), sutured, and/or otherwise secured such that cell growth mixture can be retained within the cavity 108 of the implantable article 100.

In various examples, additional cell growth mixture can be introduced into the cavity 108 of the implantable article 102. The additional cell growth mixture can be added prior to cutting the implantable article to a desired length and/or sealing the open end 104. Upon introduction of the cell growth mixture to the cavity 108 of the membrane 102 of the implantable article 100, a size of the membrane 102 of the implantable article 100 can further increase which can increase a friction fit of the membrane 102 and surrounding tissue, increase diffusion of cell growth mixture through the membrane 102, and/or increase a volume of the cavity 108. As shown in FIG. 3F, a second expandable portion 310b of the membrane 102 can increase in size responsive to the additional cell growth mixture being introduced to the cavity 108 of the implantable article 100. The second expandable portion 310b can be positioned within the tendon 322 or on an oppositely disposed surface of the tendon 322 than the expandable portion 110a is positioned. The multiple expandable portions 110a, 310b can increase the contact surface area between the membrane 102 and the tendon 322 which can promote repair of the tendon 322 and/or increase a strength of the friction fit of the implantable membrane 100 and the surrounding tissue.

Following the procedure to repair tendon 322, the insertion guide 338 can be removed and incisions caused by the procedure can be closed. The implantable device 100 can remain in communication with the base structure and/or attachment structure after the procedure to repair tendon 322 and can diffuse cell growth mixture into the surrounding tissue for a period of time. The implantable device 100, over time, can be dissolved and/or reabsorbed by the humerus 326, the tendon 322, and/or other surrounding elements.

Figure 4A:
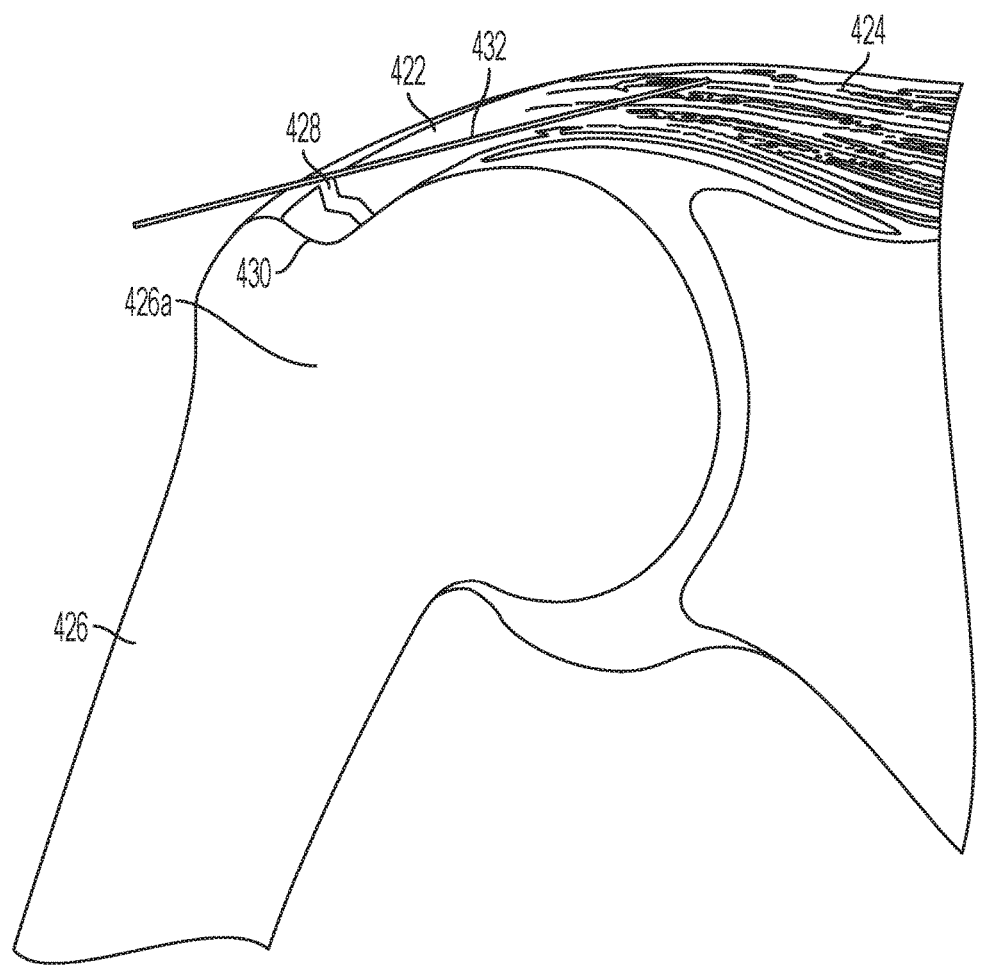
FIGS. 4A-E illustrate schematic diagrams of various steps in a method for repairing an attachment structure with the implantable article in a second orientation according to the present disclosure.

Referring to FIGS. 4A-E, the implantable article 100 can be configured to repair a tendon 422 connecting the corresponding supra-spinatus muscle 424 to the humerus 426. The tendon 422 is shown as ruptured at a location 428. As illustrated in FIG. 4A, the tendon 422 can be moved (e.g., pulled, pushed) until the tendon 422 is substantially aligned with an attachment location 430 on a humeral head 426a of the humerus 426.

A guide wire 432 can be introduced into and through the tendon 422 and then to the supra-spinatus muscle 424. The guide wire 432 can facilitate the insertion of the implantable device 100 in a desired position and/or orientation relative to the tendon 422.

Figure 4B:
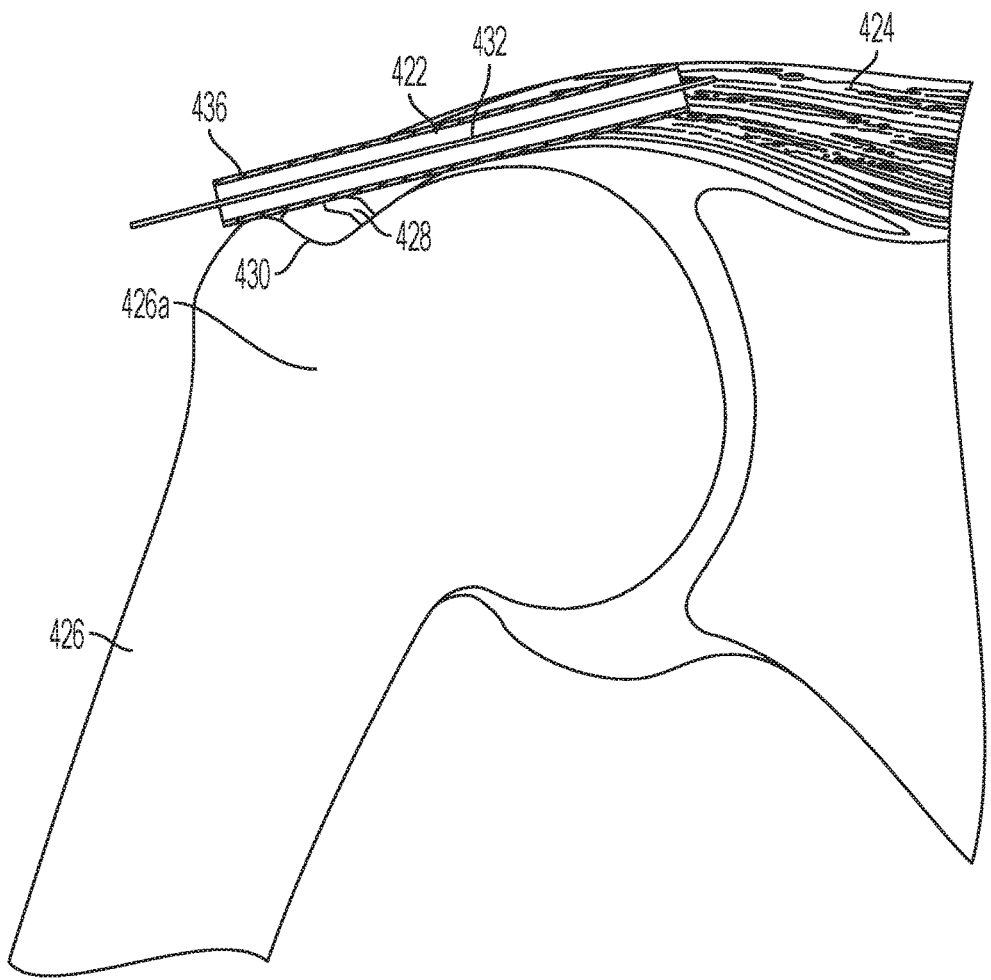

As illustrated in FIG. 4B, a dilator 436 can be substantially aligned with the guide wire 432 and advanced along the guide wire 432 in order to deform tissue surrounding the guide wire 432 including the tendon 422 and/or supra-spinatus muscle 424 in order to create a channel (not shown) configured to receive the implantable article 100.

Figure 4C:
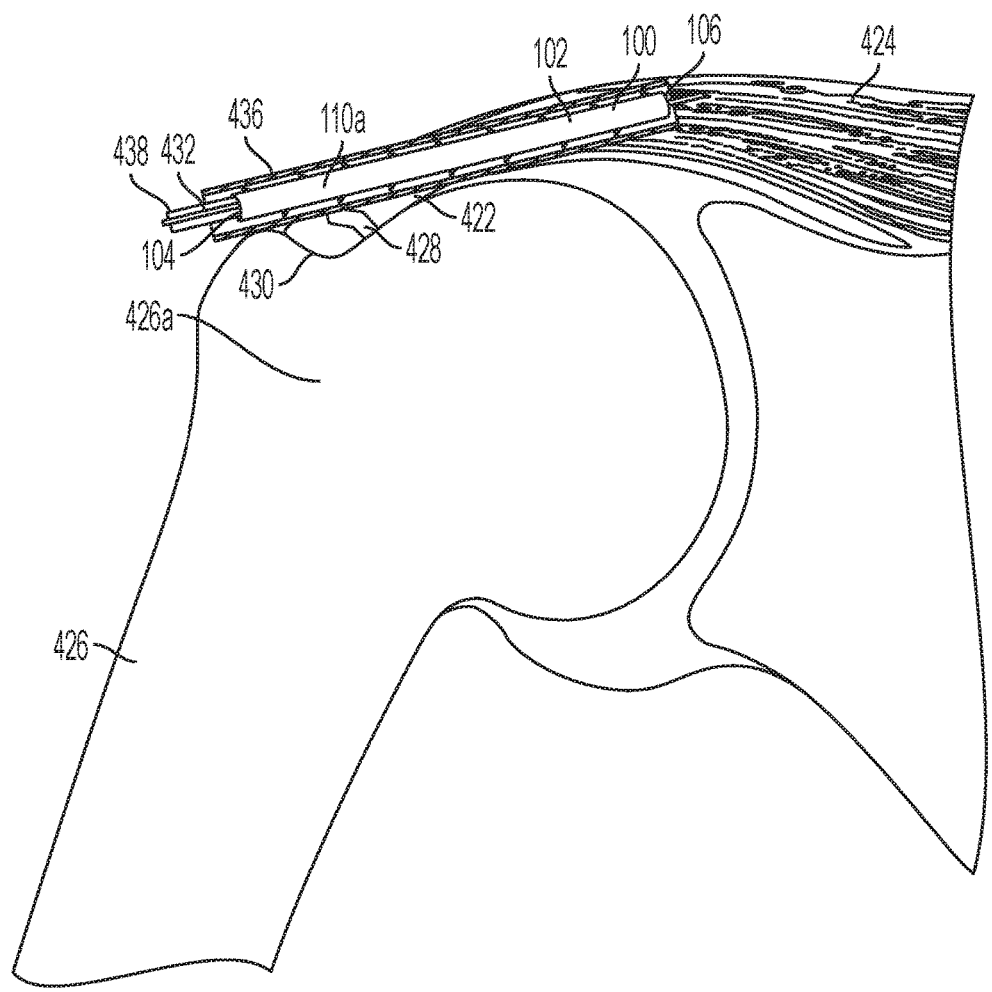

The dilator 436 can remain on the guide wire 432 and in the tissue while another device can be inserted within the dilator 436. As illustrated in FIG. 4C, an insertion guide 438 can be configured to introduce the implantable article 100 to the supra-spinatus muscle 424. The implantable article 100 can be disposed on a tip of the insertion guide 438 and the insertion guide 438 and implantable article 100 together can be advanced into the tendon 422 and supra-spinatus muscle 424 utilizing the guide wire 432. The insertion guide 438 and implantable article 100 can be advanced through the dilator 436 and the dilator 436 can be removed thereafter. The insertion guide 438 can comprise an internal cavity configured to receive the guide wire 432 and the implantable article 100 can comprise a bore on the closed end 106 configured to receive the guide wire 432. The implantable article 100 can comprise retainers 160 (not shown in FIGS. 4C-E) configured to inhibit or prevent removal of the implantable device 100 from the tendon 422 and/or supra-spinatus muscle 424.

Figure 4D:
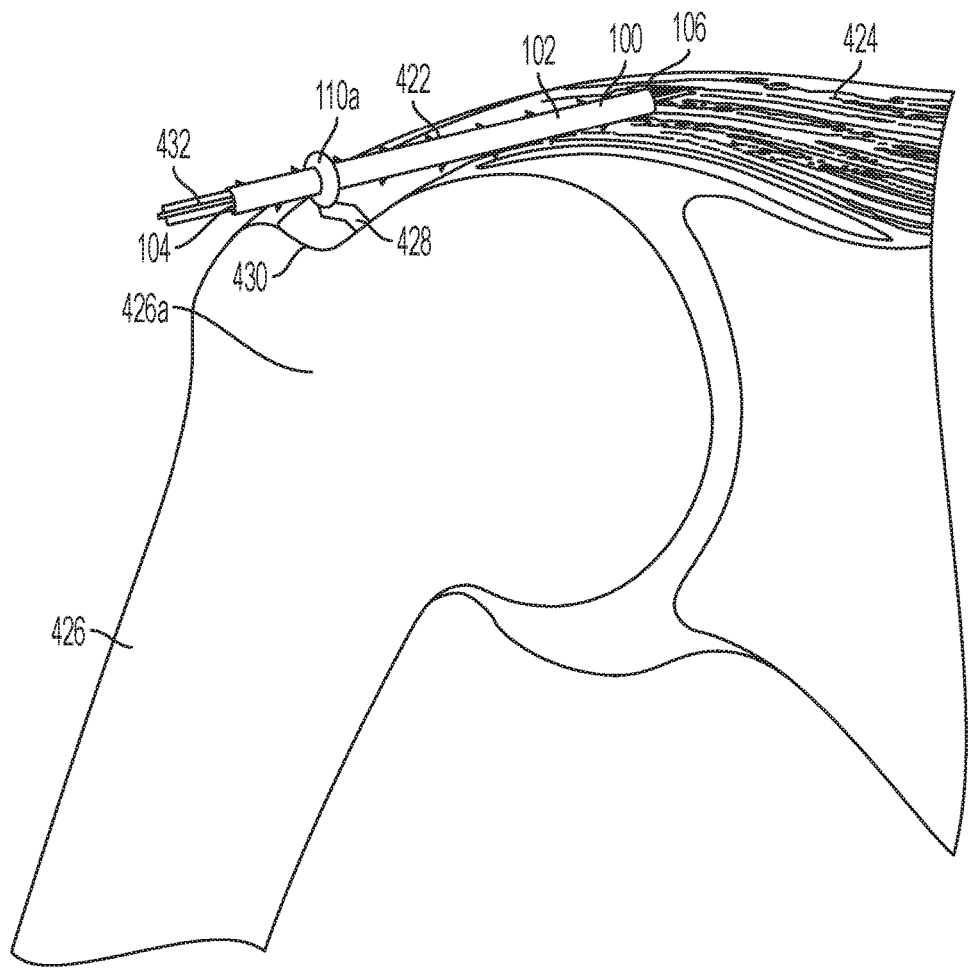

Upon inserting the implantable article 100 to a desired location, the guide wire 432 can be removed prior to an introduction of cell growth mixture into the cavity 108. Then, the cell growth mixture can be introduced into the cavity 108 of the implantable article 100 by the insertion guide 438. Upon introduction of the cell growth mixture to the cavity 108 of the membrane 102 of the implantable article 100, a size of the membrane 102 of the implantable article 100 can increase which can increase a friction fit of the membrane 102 and surrounding tissue, increase diffusion of cell growth mixture through the membrane 102, and/or increase a volume of the cavity 108. As shown in FIG. 4D, the expandable portion 110a can increase in size responsive to the cell growth mixture being introduced to the cavity 108 of the implantable article 100.

Figure 4E:
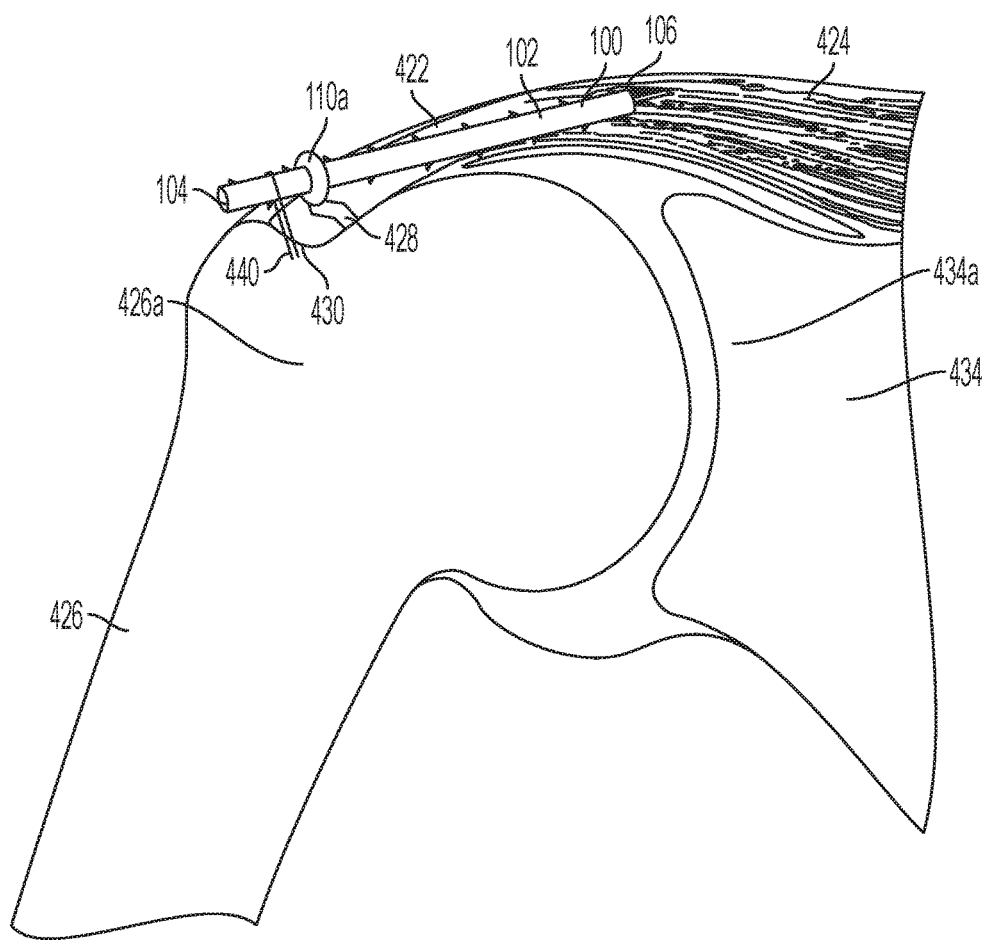

The membrane 102 of the implantable article 100 can be cut to a desired length. As illustrated in FIG. 4E, the implantable article 100 can be attached to the humerus 426 by an anchor 440. The anchor 440 can be attached prior to, during, and/or after filling the implantable article with cell growth mixture. The anchor 440 can attach the open end 104 of the implantable article to the humerus 446. Additional anchors can be installed as needed to attach the implantable article to the tendon 422 and/or the humerus 446; or attach the tendon 422 to the humerus 446.

Following the procedure to repair tendon 422, the insertion guide 438 can be removed and incisions caused by the procedure can be closed. The implantable device 100 can remain in communication with the base structure and/or attachment structure after the procedure to repair tendon 422 and can diffuse cell growth mixture into the surrounding tissue for a period of time. The implantable device 100, over time, can be dissolved and/or reabsorbed by the humerus 426, the tendon 422, and/or other surrounding elements.

In various examples, a quantity of implantable devices used to repair a degraded attachment structure can be 2 or greater implantable devices, such as, for example, 3 or greater, 4 or greater, 5 or greater, 6 or greater, 10 or greater, or 15 or greater implantable devices. A quantity of implantable devices used to repair a degraded attachment structure can be 20 or less implantable devices, such as, for example, 15 or less, 10 or less, 6 or less, 5 or less, 4 or less, or 3 or less implantable devices. A quantity of implantable devices used to repair a degraded attachment structure can be in a range of 1 to 20 implantable devices, such as, for example, 1 to 3 implantable devices. In various examples comprising a plurality of implantable devices, the implantable devices can be positioned in attachment locations in a base structure which are arranged in two or more rows and each row can be positioned offset from an adjacent row (e.g., staggered). The offset positioning can limit undesired fractures in the base structure.

In various examples comprising at least two implantable devices, a single staple can be driven into in two proximally positioned anchors (e.g., one leg in each implantable device). In various examples comprising two or greater implantable devices, a connecting member (e.g., tape) can be attached to each anchor of each implantable device utilizing, for example, a biocompatible adhesive between the connecting member and each anchor. The connecting member can provide a large contact surface which can contact the attachment structure and maintain a position and/or orientation of the attachment structure.

Figure 5:
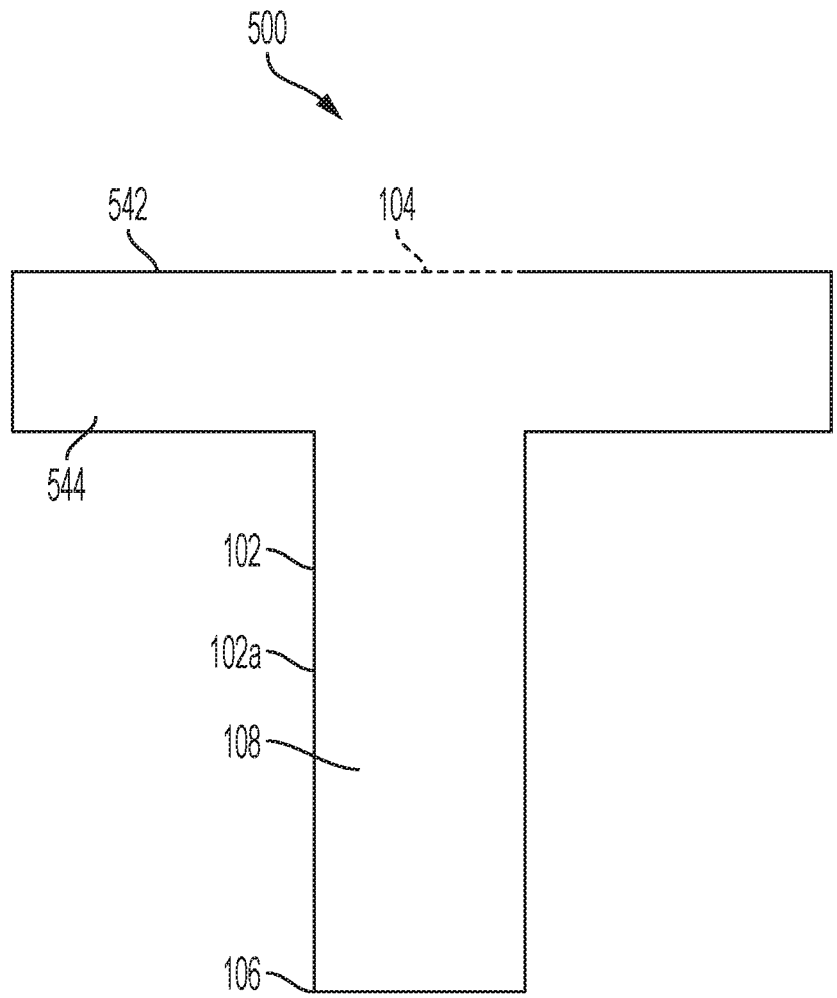
FIG. 5 illustrates an implantable article comprising a flange according to the present disclosure.

As illustrated in FIG. 5, an implantable article 500 can be configured with a flange 542. For example, the implantable article 500 can be substantially button shaped. The flange 542 can comprise biological material. The flange 542 can comprise a generally round shape, a generally elliptical shape, or a polygon shape (e.g., a tape-like shape). For example, the flange 542 can be formed by attaching two layers of a biological material to each other to form an annular cavity 544 configured to receive cell growth mixture. The flange 542 can comprise various geometric shapes configured to avoid any edges that may irritate surrounding tissues. For example, the flange 542 may not have any corners and the flange 542 may comprise a generally torus shape. In various other examples, the flange 542 may have a corner.

The flange 542 can increase the surface area of the implantable article 500 which can promote the repair of the attachment structure. The implantable article 500 can be installed in a variety of positions and/or orientations. For example, the implantable article 500 can be inserted into a base structure and the flange 542 can be positioned between the base structure and the attachment structure. The flange 522 can be positioned flush against a base structure. In various other examples, the implantable article 500 can be inserted into an attachment structure and the flange 542 can be positioned between the base structure and the attachment structure. The membrane 102 and/or flange 544 of implantable article 500 can be secured to an attachment structure and/or base structure with an anchor.

Figure 6:
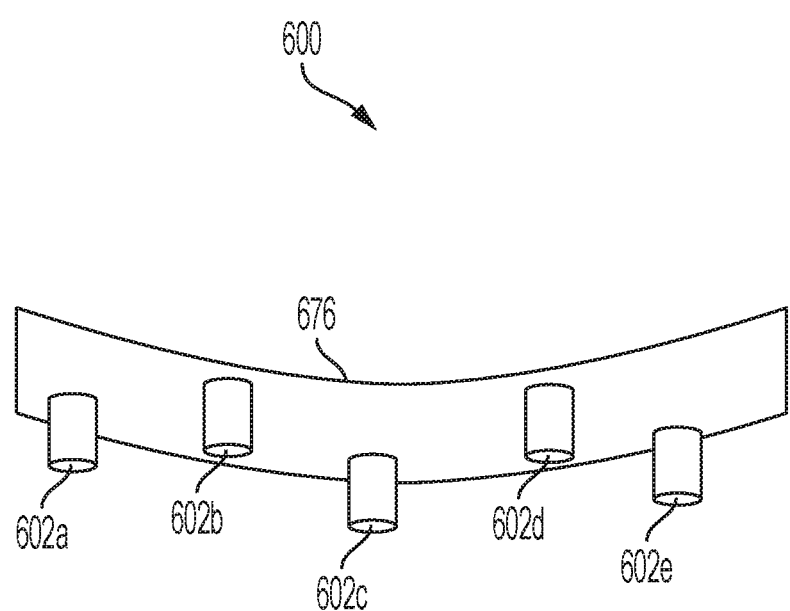
FIG. 6 illustrates an implantable article comprising a plurality of membrane projections according to the present disclosure.

As illustrated in FIG. 6, an implantable article 600 comprising a connector 676 and a plurality of membrane projections 602*a-e*. Each membrane projection 602*a-e* can be configured as membrane 102 of FIG. 1. For example, each membrane projection 602*a-e* can be attached to a base structure and/or attachment structure. The connector 676 can join the plurality of membrane projections 602*a-e* to one another and increase the contact surface area between the implantable article 600 and the attachment structure. The increased contact surface area can distribute attachment forces across the attachment structure and can limit, if not prevent, additional degradation to the attachment structure. The membrane projections 602*a-e* can be positioned in offset rows along the connector 676. The offset rows can minimize undesired fractures in a base structure in which they are installed. Additionally, the offset rows can increase a spacing distance between adjacent membrane projections 602*a-e* while maintaining a compact overall implantable article 600 and a desired quantity of membrane projections 602*a-e*. For example, the membrane projections 602*a-e* can be spaced a distance in a range of 0.1 inches to 1 inch.

The implantable article 600 can be integrally formed with the connector 676 or the membrane projections 602*a-e* can be attached to the connector 676 via a biocompatible adhesive. In various examples, the implantable article 600 can be integrally formed from a frozen mixture of cross linked collagen fibers in water and lyophilizing the frozen mixture to remove the water molecules. The connector 676 can be a tape.

Figure 7:
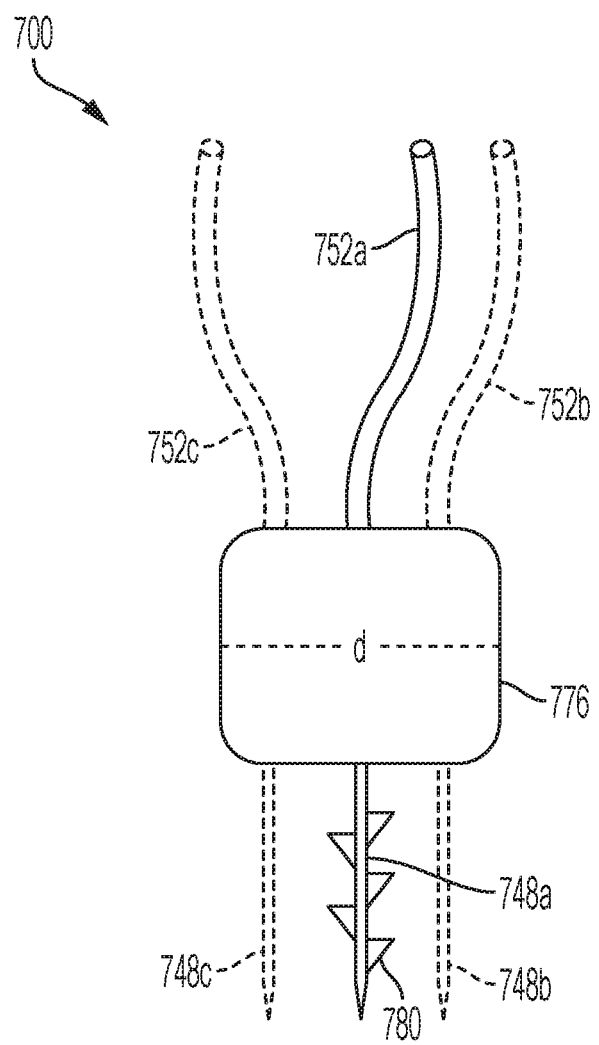
FIG. 7 illustrates a schematic view of an implantable article comprising an insertion tip, a reservoir, and a tube according to the present disclosure.

As illustrated in FIG. 7, an implantable article 700 comprising a reservoir 746, a an insertion tip 748*a*, and a tube 752*a* is provided. The insertion tip 748*a* can be configured to be attached to a muscle and/or an attachment structure. For example, the insertion tip 748*a* can be inserted into and retained by a muscle and/or an attachment structure. The insertion tip 748*a* can comprise biological material and can comprise retainers 780 disposed on an outer surface. The retainers 780 can enable facile insertions of the insertion tips 748*a* into a muscle and/or an attachment structure. The retainers 780 can inhibit or prevent removal of the insertion tip 748*a* from the muscle and/or the attachment structure. The insertion tip 748*a* can be attached to the muscle and/or attachment structure to maintain a position and/or orientation of the reservoir 746 relative to the muscle and/or attachment structure.

The insertion tip 748*a* can comprise a cavity configured to receive the cell growth mixture and the insertion tip 748*a* can increase in size responsive to the receipt of the cell growth mixture. The increase in size of the insertion tip 748*a* can increase the strength of attachment between the insertion tip 748*a* and the muscle, the base structure, and/or the attachment structure. In various examples, the implantable article 700 can comprise at least two insertion tips, such as, for example, insertion tip 748*a* and insertion tip 748*b*, or the implantable article can comprise at least three insertion tips, such as, for example, insertion tip 748*a*, insertion tip 748*b*, and insertion tip 748*c*.

A muscle can repair deformations caused by the insertion tips 748*a-c* faster than an attachment structure could repair deformations caused by the insertion tips 748*a-c*. Thus, in various examples, the insertion tips 748*a-c* can be inserted into a muscle which can limit, if not prevent, undesired additional degradation to the attachment structure. For example, the insertion tips 748*a-c* can be inserted into the muscle corresponding to a tendon. The implantable member 700 can be installed into a side of the corresponding muscle proximal to the bone which can minimize, if not eliminate, additional degradation of the tendon while enabling the reservoir 746 to be position proximal to a degradation present in the tendon.

The reservoir 746 can be in fluid communication with each insertion tip 748*a-c* and can receive cell growth mixture. For example, each insertion tip 748*a-c* can comprise an open end adjacent to the reservoir 746 and an oppositely disposed closed end configured to attach to a muscle and/or the attachment structure. The open end of each insertion tip 748*a-c* can receive the cell growth mixture from the reservoir 746. Each insertion tip 748*a-c* can comprise a cavity extending from their respective open end to their respective closed end.

The reservoir 746 can comprise biological material and can comprise a dimension, d, which corresponds to a dimension of an attachment structure. For example, a tendon connecting the supraspinatus muscle to the humerus can comprise a width of 1.5 cm to 2.5 cm, when pressed against a base structure and thus, the dimension, d, may be 1.5 cm to 2.5 cm. In various examples, dimension, d, may be in a range of 1 cm to 4 cm.

The tube 752*a* can be in fluid communication with the reservoir 746 and can receive a cell growth mixture. The tube 752*a* can transport the cell growth mixture into the reservoir 746 and, in various examples, the insertion tips 748*a-c*. A length of the tube 752*a* can be trimmed to a desired length which can be after the cell growth mixture has been transported to the reservoir 746 and/or the insertion tips 748*a-c*. The tube 752*a* can be attached to the base structure to maintain a position and/or orientation of the reservoir 746 relative to the base structure. In various examples comprising trimming the length of tube 752*a*, the tube 752*a* can be attached to the base structure after trimming or the tube 752*a* can be attached to the base structure before trimming. In various examples, the tube 752*a* can be attached to a thread and/or a tape and the thread and/or tape can be attached to the base structure to secure the implantable article 700. In various examples, the implantable article 700 can comprise at least two tubes, such as, for example, tube 752*a* and tube 752*b*, or the implantable article can comprise at least three tubes, such as, for example, tube 752*a*, tube 752*b*, and tube 752*c*.

The position of the reservoir 746 can change depending on the attachment locations of the insertion tips 748*a-c* and the tubes 752*a-c*. In various examples, the reservoir 746 is not directly attached to the muscle, base structure, and/or attachment structure by an anchor. In various other examples, the reservoir 746 is directly attached to at least one of the muscle, the base structure, and attachment structure by an anchor.

The implantable article 700 can comprise various other elements, such as, for example, a check valve positioned within the insertion tips 748*a-c* and/or tubes 752*a-c*. The check valve can maintain a quantity of cell growth mixture in the insertion tips 748*a-c* and an increased size of the insertion tips 748*a-c* which inhibit de-attachment of the implantable article 700 while attaching the implantable article 700 to a base structure or during contraction of a corresponding muscle attached to the tendon. For example, maintaining the increased size of the insertion tips 748*a-c* can maintain a friction fit between the insertion tips 748*a-c* and a base structure and/or attachment structure.

The articles and methods according to the present disclosure can be for minimally-invasive surgery. As used herein, the term "surgery" refers to any type of tissue manipulation which penetrates the skin, and which involves anything more than a single type of medical device, such as, for example, a guide wire, an insertion guide, a dilator, a needle, a tamping device, and/or a trocar.

Figure 8:
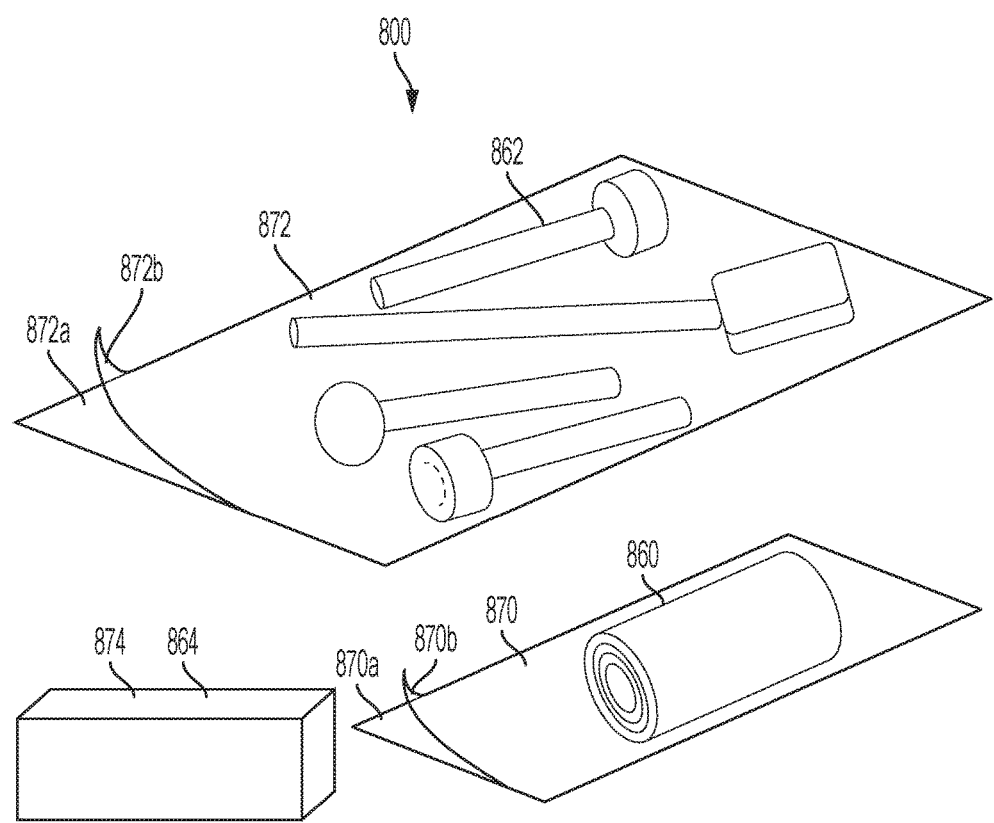
FIG. 8 illustrates a perspective view of a surgical kit according to the present disclosure.

As illustrated in FIG. 8, a surgical kit 800 is provided which can be used to repair an attachment structure. The surgical kit 800 comprises various components, such as, for example, a dilator tube set 860, a tamping device set 862, and a biological material set 864. The dilator tube set 860 can comprise a single dilator tube or two or more dilator tubes. In examples comprising two or more dilator tubes, each tube can comprise a different diameter and/or taper to enable efficient creation of a tunnel in soft tissue.

Figure 10:
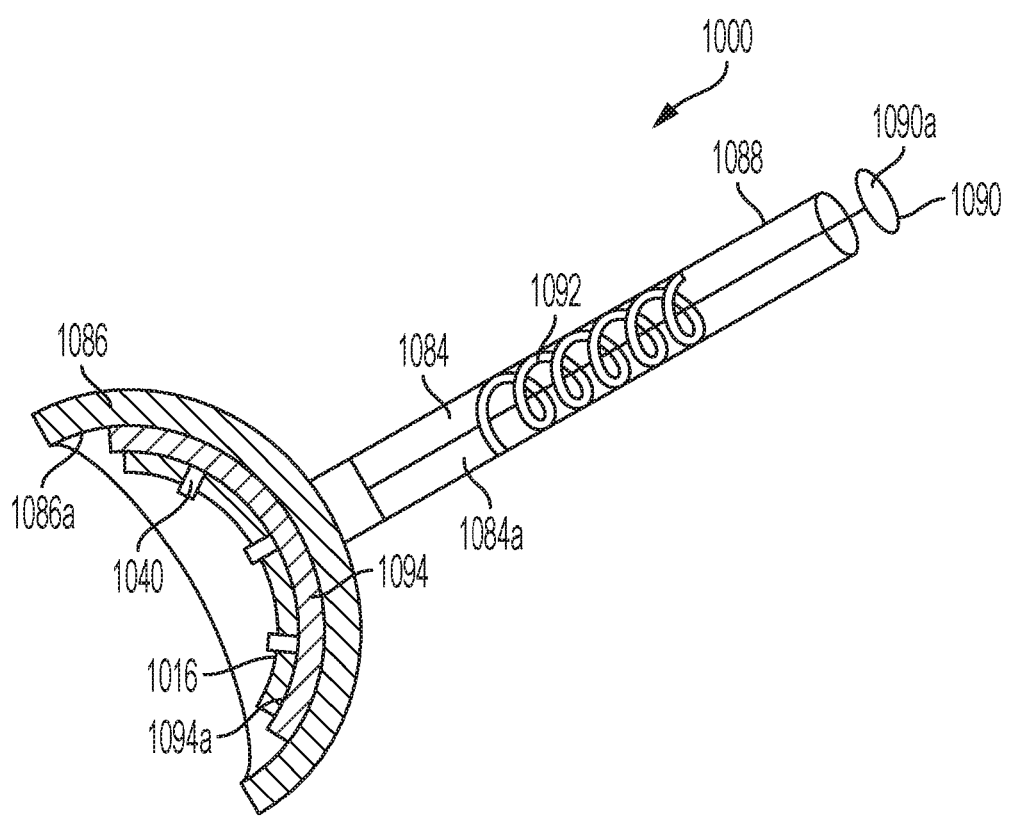
FIG. 10 illustrates a cross-sectional side view of a tamping device according to the present disclosure.

The tamping device set 862 can comprise a single tamping device or two or more tamping devices. The tamping device set 862 can be configured to manipulate soft tissues, move and/or press a attachment structure, move and/or press a implantable device 100, 400, 500, 600, and/or provide control over insertion of an anchor into the implantable device 100, 400, 500, 600, a base structure, and/or an attachment structure. The tamping device set 862 can comprise tamping devices with variously shaped heads, such as, for example, planar, concave, convex, or angled. In various examples, the tamping device set 862 can comprise a tamping device with a textured surface. In various examples, the tamping device set 862 can comprise tamping device 1000 as illustrated in FIG. 10.

For example, the tamping device set 862 can comprise, for example, a suction tool as described in U.S. patent application Ser. No. 15/482,696. The plunger of the suction tool can comprise a spring activated plunger. The actuator end of the tamping device can comprise a diameter in a range of 0.1 centimeters to 2 centimeters, such as, for example, 0.8 centimeter to 1 centimeter.

In various examples, the tamping device set 862 can comprise, for example, a tibial tamping tool as described in U.S. patent application Ser. No. 15/482,696. The tibial tamping tool can comprise a spring activated head component. The head component of the tibial tamping tool can be attached to the head component at an angle in a range of 15 degrees to 30 degrees, such as, for example, 15 degrees to 20 degrees or 20 degrees to 30 degrees. The tibial tamping tool can be attached to the head component in the center of the head component or an end of the head component.

The biological material set 864 can comprise at least one of the implantable devices 100, 500, 600, 700 and/or raw material (e.g., biological material) for producing at least one of the implantable devices 100, 500, 600, 700. In examples comprising two or more implantable devices, each implantable device can comprise a different size, shape, and/or configuration.

The dilator tube set 860 can be sealed within a sterile envelope 870, the tamping device set 862 can be sealed within a sterile envelope 872, and the biological material set 864 can be sealed within a sterile envelope 874. Each sterile envelope 870, 872, 874 can be opened prior to use. In various examples, at least two of the dilator tube set 860, tamping device set 862, and biological material 864 are stored within the same sterile envelope.

Each envelope 870, 872 can be formed from a backing layer 870*a*, 872*a*, and a sealing layer 870*a*, 870*b* attached to the respective backing layer 870*a*, 872*a* around the periphery to create a seal. Each backing layer 870*b*, 872*b* can be opaque and each sealing layer 870*a*, 870*b* can be transparent. The transparent sealing layer 870*a*, 870*b* can enable quick identification of contents within each envelope 870, 872. In various examples, each envelope 870, 872 can be vacuum packed. The layers 870*a*, 870*b*, 872*a*, 872*b* can comprise a polymer. The upturned corners of layers 870*b*, 872*b* shown in FIG. 8 are for illustration purposed only and should not be considered limiting.

The envelope 874 can comprise a polymer, a metal, and/or a metal alloy. The envelope 874 can provide a sterile environment for the enclosed contents. The biological material set 864 can be included as part of the surgical kit 800 or separate from the surgical kit 800 as an independent component which can be added at a later time to the container that holds other components of the surgical kit 800.

Figure 9:
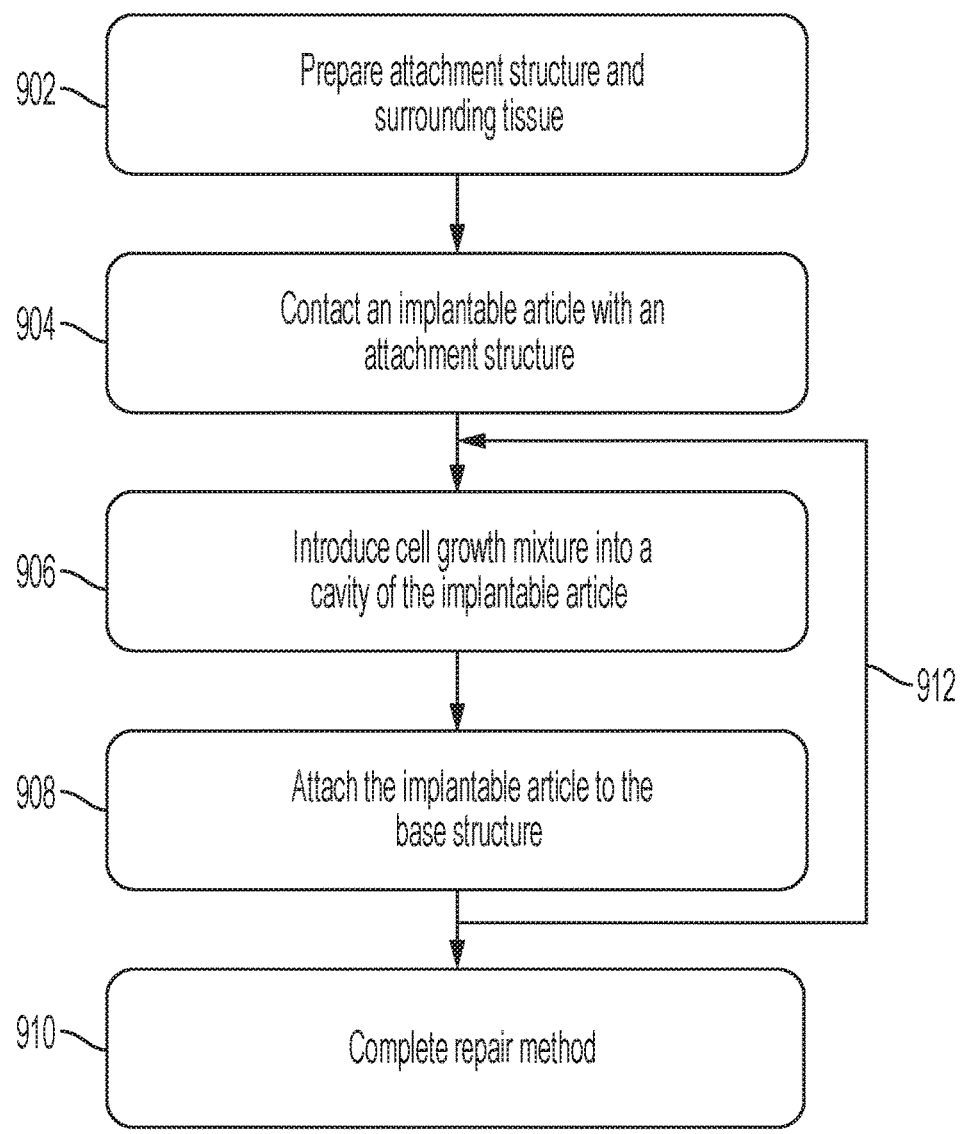
FIG. 9 illustrates a flow chart for a method for repairing an attachment structure with an implantable device according to the present disclosure.

Referring to FIG. 9, a method for repairing an attachment structure is provided. As illustrated, an attachment structure that is degraded can be prepared for surgery and optionally, the surrounding tissue can be prepared for surgery, 902. For example, at least one of the following may occur: the surrounding tissue may be manipulated (e.g., change the position and/or orientation of the humerus relative to the scapula); movement of a base structure can be limited (e.g., a joint can be secured in a desired position); the surrounding tissue (e.g., skin) may be disinfected and/or sterilized; anesthesia may be administered (local and/or general); an initial incision may be made in the surrounding tissue; a guide wire may be inserted into the attachment structure and/or surrounding tissue; a dilator may be inserted; a bore may be formed in the bone; a laser may be used to create nano-fractures on a surface of a bone which can enable diffusion of the cell growth mixture into the bone and/or enable diffusion of cells out of the bone; and various other procedures may occur.

An implantable article according to the present disclosure can be contacted with the attachment structure, 904. For example, the implantable article according to the present disclosure can contact the attachment structure by inserting the implantable article according to the present disclosure into the attachment structure and/or positioning the implantable article according to the present disclosure adjacent to the attachment structure. An insertion guide may be used to insert and/or position the implantable article according to the present disclosure. In various examples, an ultrasound or fluoroscope may be used to guide the insertion and/or positioning of the implantable article according to the present disclosure. In various examples, a guide wire may not be used if an ultrasound or fluoroscope device is used.

Cell growth mixture can be introduced into a cavity of the implantable article according to the present disclosure, 906. In examples where an insertion guide comprising a catheter is used, the catheter can be used to introduce the cell growth mixture into the cavity of the implantable article and fill the cavity with the cell growth mixture. Introduction of the cell growth mixture to the cavity can increase the size of an expandable portion of a membrane of the implantable article according to the present disclosure which can increase a surface area of the implantable article according to the present disclosure. In various examples where the insertion guide is a balloon catheter, a balloon of the balloon catheter can increase the size of the expandable portion and back-fill the expandable portion with the cell growth mixture.

The implantable article according to the present disclosure can be attached to the base structure with an anchor, 908. The anchor can be inserted through various portions of the implantable article according to the present disclosure. For example, the anchor can be inserted through a closed end of the implantable article according to the present disclosure and then the base structure. The anchor can be installed before or after the introduction of the cell growth mixture to the cavity. The introduction of cell growth mixture to the cavity and the attachment of the implantable article to the base structure can be repeated as necessary, 912.

Thereafter, various other procedures may occur and the repair of the attachment structure method may be complete, 910. For example, any of the various medical devices (e.g., guide wires, dilators, catheters) may be removed and any incisions may be closed.

Referring to FIG. 10, a tamping device 1000 is provided. The tamping device 1000 can comprise a shaft 1084, a head portion 1086, and a handle portion 1088. The head portion can comprise a diameter in a range of 0.1 centimeters to 2 centimeters, such as, for example, 0.8 centimeter to 1 centimeter. The shaft 1084 can operatively couple the head portion 1086 to the handle portion 1088. The shaft 1084 can comprise a cavity 1084a configured to receive a plunger 1090. The plunger 1090 can be under tension by a spring 1092. For example, the plunger 1090 is shown in a first position. Upon activation of the plunger 1090 by pushing a first end 1090a of the plunger 1090, the plunger 1090 can move through the cavity 1084a to a second position closer to the head portion 1086. Upon release of the plunger 1090 from the second position to the first position, a vacuum force can be created on a first side 1086a of the head portion 1086. Activating the plunger 1090 and moving the plunger 1090 from the first position to the second position can release the vacuum force.

The tamping device 1000 can be used to apply a membrane 1094 to an attachment structure. For example, as illustrated, a membrane 1094 comprising a biological material can be adhered to the first side 1086a of the head portion 1086 by the vacuum force. The membrane 1094 can comprise anchors 1040. A layer of cell growth mixture 1016 can be applied to a side 1094a of the membrane 1094. Thereafter, the membrane 1094 and cell growth mixture 1016 can be applied to a partial or complete rupture of the attachment structure. The tamping device 1000 can apply a force to the anchors 1040 in the membrane 1094 to secure the anchors 1040 to the attachment structure and/or a base structure thereby securing the membrane 1094 and the layer of cell growth mixture 1016 to the attachment structure and/or a base structure. Thereafter, the plunger 1090 can be activated from the first position to the second position to release the membrane 1094 and the layer of cell growth mixture 1016 from the tamping tool 1000 and the tamping tool 1000 can be separated from the membrane 1094.

One skilled in the art will recognize that the herein described compositions, articles, methods, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken as limiting.

Various aspects of the invention according to the present disclosure include, but are not limited to, the aspects listed in the following numbered clauses.

1. An implantable article configured for attaching at least one of a tendon and a ligament to at least one of bone and cartilage, the implantable article comprising:
    a membrane comprising a biological material that promotes cell growth, the membrane comprising:
        an open end configured to receive a cell growth mixture;
        a closed end configured to be attached to the at least one of bone, cartilage, a tendon, and a ligament; and
        a cavity extending from the open end to the closed end, the cavity is configured to receive a cell growth mixture from the open end.
2. The implantable article of clause 1, wherein the membrane comprises a generally cylindrical shape or a generally elliptical shape.
3. The implantable article of any one of clauses 1-2, wherein the biological material comprises at least one of a placental membrane, a collagen membrane, a carbohydrate matrix, a biocompatible polymer membrane, and a biologically derived membrane.
4. The implantable article of any one of clauses 1-3, wherein the open end is configured to receive a dowel.
5. The implantable article of any one of clauses 1-4, further comprising a flange attached to the membrane, the flange comprising biological material and a flange cavity configured to receive the cell growth mixture.
6. The implantable article of any one of clauses 1-5, further comprising retainers on an outer surface of the membrane.
7. An assembly of the implantable article of claim 1 and an anchor.
8. The assembly of clause 7, wherein the anchor comprises at least one of a staple, a pin, a fastener, a suture, a dowel, and an adhesive.
9. The assembly of clause 8, wherein the anchor comprises a dowel.
10. The assembly of clause 9, wherein the dowel is formed from additive manufacturing.
11. An assembly of the implantable article of claim 1 and a cell growth mixture or the assembly of any one of clauses 7-10 and a cell growth mixture.
12. The assembly of clause 11, wherein the cell growth mixture comprises at least one of stem cells, platelets, and spun fat.
13. A surgical kit comprising the implantable article of any one of clauses 1-6, a dilator tube set, and a tamping device set.

14. A method for repairing at least one of a tendon and a ligament comprising:
  contacting an implantable article with the at least one of the tendon and the ligament, the implantable article comprising:
    a membrane comprising a biological material that promotes cell growth, the membrane comprising:
      an open end configured to receive a cell growth mixture;
      a closed end configured to be attached to the at least one of bone, cartilage, a tendon, and a ligament; and
      a cavity extending from the open end to the closed end, the cavity is configured to receive a cell growth mixture from the open end;
  introducing a cell growth mixture into the cavity of the implantable article; and
  attaching the implantable article to at least one of bone and cartilage with an anchor.

15. The method of clause 14, wherein attaching the implantable article to the at least one of bone and the cartilage further comprises:
  forming a bore in the at least one of bone and cartilage;
  inserting the closed end of the membrane into the bore; and
  wherein the anchor comprises a dowel, inserting the dowel through the cavity of the implantable article and creating a friction fit between the membrane and the bore.

16. The method of clause 14,
  wherein contacting an implantable article with the at least one of the tendon and the ligament comprises inserting the closed end of the membrane into at least one of the tendon and the ligament; and
  wherein attaching the implantable article to the at least one of bone and the cartilage comprises attaching the open end of the membrane to the at least one of the bone and the cartilage with the anchor.

17. The method of any one of clauses 14-16, wherein introducing the cell growth mixture into the cavity further comprises increasing a size of the implantable article.

18. The method of any one of clauses 14-17, wherein the at least one of the tendon and the ligament comprises at least one of an anterior cruciate ligament and a tendon which attaches the supra-spinatus muscle to a humerus.

19. An implantable article configured for attaching at least one of a tendon and a ligament to at least one of bone and cartilage, the article comprising:
  a first membrane comprising a biological material that promotes cell growth, the first membrane comprising:
    a first open end configured to receive a cell growth mixture;
    a first closed end configured to be attached to the at least one of the bone and the cartilage; and
    a first cavity extending from the first open end to the first closed end, the first cavity is configured to receive the cell growth mixture from the first open end;
  a second membrane comprising the biological material, the second membrane comprising:
    a second open end configured to receive the cell growth mixture; and
    a second closed end configured to be attached to the at least one of the bone and the cartilage; and
    a second cavity extending from the second open end to the second closed end, the second cavity is configured to receive the cell growth mixture from the second open end; and
  a flange connecting the first membrane to the second membrane.

20. An implantable article configured for attaching at least one of a tendon and a ligament to at least one of bone and cartilage, the article comprising:
  an insertion tip comprising a biological material that promotes cell growth, the insertion tip comprising:
    an open end configured to receive a cell growth mixture;
    a closed end configured to be attached to at least one of a muscle, a tendon, and a ligament; and
    a cavity extending from the open end to the closed end, the cavity is configured to receive a cell growth mixture from the open end;
  a reservoir comprising the biological material, the reservoir is in fluid communication with the insertion tip and the reservoir is configured to receive the cell growth mixture; and
  a tube in fluid communication with the reservoir, the tube is configured to receive the cell growth mixture, transport the cell growth mixture to the reservoir, and to be attached to the at least one of the bone and the cartilage. With respect to the appended claims, those skilled in the art will appreciate that recited operations therein may generally be performed in any order. Also, although various operational flows are presented in a sequence(s), it should be understood that the various operations may be performed in other orders than those which are illustrated or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

Various features and characteristics are described in this specification to provide an understanding of the composition, structure, production, function, and/or operation of the invention, which includes the disclosed compositions, coatings, and methods. It is understood that the various features and characteristics of the invention described in this specification can be combined in any suitable manner, regardless of whether such features and characteristics are expressly described in combination in this specification. The Inventors and the Applicant expressly intend such combinations of features and characteristics to be included within the scope of the invention described in this specification. As such, the claims can be amended to recite, in any combination, any features and characteristics expressly or inherently described in, or otherwise expressly or inherently supported by, this specification. Furthermore, the Applicant reserves the right to amend the claims to affirmatively disclaim features and characteristics that may be present in the prior art, even if those features and characteristics are not expressly described in this specification. Therefore, any such amendments will not add new matter to the specification or claims and will comply with the written description, sufficiency of description, and added matter requirements.

The invention(s) described in this specification can comprise, consist of, or consist essentially of the various features and characteristics described in this specification. The terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. Thus, a composition, coating, or method that "comprises," "has," "includes," or "contains" one or more features and/or characteristics possesses those one or more features and/or characteristics but is not limited to possessing only those one or more features and/or characteristics. Likewise, an element of a composition, coating, or process that "comprises," "has," "includes," or "contains" one or more features and/or characteristics possesses those one or more features and/or characteristics but is not limited to possessing only those one or more features and/or characteristics and may possess additional features and/or characteristics.

Any patent, publication, or other document identified in this specification is incorporated by reference into this specification in its entirety unless otherwise indicated but only to the extent that the incorporated material does not conflict with existing descriptions, definitions, statements, illustrations, or other disclosure material expressly set forth in this specification. As such, and to the extent necessary, the express disclosure as set forth in this specification supersedes any conflicting material incorporated by reference. Any material, or portion thereof, that is incorporated by reference into this specification, but which conflicts with existing definitions, statements, or other disclosure material set forth herein, is only incorporated to the extent that no conflict arises between that incorporated material and the existing disclosure material. Applicant reserves the right to amend this specification to expressly recite any subject matter, or portion thereof, incorporated by reference. The amendment of this specification to add such incorporated subject matter will comply with the written description, sufficiency of description, and added matter requirements.

While the present disclosure provides descriptions of various specific aspects for the purpose of illustrating various aspects of the present disclosure and/or its potential applications, it is understood that variations and modifications will occur to those skilled in the art. Accordingly, the invention or inventions described herein should be understood to be at least as broad as they are claimed and not as more narrowly defined by particular illustrative aspects provided herein.

What is claimed is:

1. An implantable article configured for attaching at least one of a tendon and a ligament to at least one of bone and cartilage, the implantable article comprising:
    a membrane comprising a biological material that promotes cell growth, the membrane comprising:
        an open end configured to receive a cell growth mixture;
        a closed end configured to be attached to at least one of the bone, the cartilage, the tendon, and the ligament; and
        a cavity extending from the open end to the closed end, the cavity is configured to receive a cell growth mixture from the open end; and
    a flange attached to the membrane, the flange comprising biological material and a flange cavity configured to receive the cell growth mixture.

2. The implantable article of claim 1, wherein the membrane comprises a generally cylindrical shape or a generally elliptical shape.

3. The implantable article of claim 1, wherein the biological material comprises at least one of a placental membrane, a collagen membrane, a carbohydrate matrix, a biocompatible polymer membrane, and a biologically derived membrane.

4. The implantable article of claim 1, wherein the open end is configured to receive a dowel.

5. The implantable article of claim 1, further comprising retainers on an outer surface of the membrane.

6. An assembly of the implantable article of claim 1 and an anchor.

7. The assembly of claim 6, wherein the anchor comprises at least one of a staple, a pin, a fastener, a suture, a dowel, and an adhesive.

8. The assembly of claim 7, wherein the anchor comprises a dowel.

9. The assembly of claim 8, wherein the dowel is formed from additive manufacturing.

10. An assembly of the implantable article of claim 1 and a cell growth mixture.

11. The assembly of claim 10, wherein the cell growth mixture comprises at least one of stem cells, platelets, and spun fat.

12. A surgical kit comprising the implantable article of claim 1, a dilator tube set, and a tamping device set.

13. A method for repairing at least one of a tendon and a ligament comprising:
    contacting an implantable article with the at least one of the tendon and the ligament, the implantable article comprising:
        a membrane comprising a biological material that promotes cell growth, the membrane comprising:
            an open end configured to receive a cell growth mixture;
            a closed end configured to be attached to at least one of bone, cartilage, the tendon, and the ligament; and
            a cavity extending from the open end to the closed end, the cavity is configured to receive a cell growth mixture from the open end;
    introducing a cell growth mixture into the cavity of the implantable article; and
    attaching the implantable article to at least one of the bone and the cartilage with an anchor.

14. The method of claim 13, wherein the at least one of the tendon and the ligament comprises at least one of an anterior cruciate ligament and a tendon which attaches the supra-spinatus muscle to a humerus.

15. The method of claim 13, wherein attaching the implantable article to the at least one of the bone and the cartilage further comprises:
    forming a bore in the at least one of the bone and the cartilage;
    inserting the closed end of the membrane into the bore; and
    wherein the anchor comprises a dowel, inserting the dowel through the cavity of the implantable article and creating a friction fit between the membrane and the bore.

16. The method of claim 13, wherein introducing the cell growth mixture into the cavity further comprises increasing a size of the implantable article.

17. The method of claim 13,
    wherein contacting an implantable article with the at least one of the tendon and the ligament comprises inserting the closed end of the membrane into the at least one of the tendon and the ligament; and
    wherein attaching the implantable article to the at least one of the bone and the cartilage comprises attaching the open end of the membrane to the at least one of the bone and the cartilage with the anchor.

18. An assembly configured for attaching at least one of a tendon and a ligament to at least one of bone and cartilage, the assembly comprising:
    a dowel configured to be pressed into a bore formed in the at least one of the bone and the cartilage for a friction fit; and
    an implantable article comprising:
        a membrane comprising a biological material that promotes cell growth, the membrane comprising:
            an open end configured to receive a cell growth mixture and the dowel;
            a closed end configured to be attached to the at least one of the bone and the cartilage; and
            a cavity extending from the open end to the closed end, the cavity is configured to receive the cell growth mixture from the open end.

19. An implantable article configured for attaching at least one of a tendon and a ligament to at least one of bone and cartilage, the article comprising:
    an insertion tip comprising a biological material that promotes cell growth, the insertion tip comprising:
        an open end configured to receive a cell growth mixture;
        a closed end configured to be attached to at least one of a muscle, a tendon, and a ligament; and
        a cavity extending from the open end to the closed end, the cavity is configured to receive a cell growth mixture from the open end;
    a reservoir comprising the biological material, the reservoir is in fluid communication with the insertion tip and the reservoir is configured to receive the cell growth mixture; and
    a tube in fluid communication with the reservoir, the tube is configured to receive the cell growth mixture, transport the cell growth mixture to the reservoir, and to be attached to the at least one of the bone and the cartilage.

20. The assembly of claim 19, wherein the dowel comprises at least one material selected from the group consisting of bone, polyether ether ketone, and apatite.

* * * * *